United States Patent
Isakov

(10) Patent No.: US 10,156,532 B2
(45) Date of Patent: Dec. 18, 2018

(54) SYSTEM AND METHOD FOR DETECTING A DEFECTIVE SAMPLE

(71) Applicant: AGENCY FOR SCIENCE, TECHNOLOGY AND RESEARCH, Singapore (SG)

(72) Inventor: Dmitry Isakov, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 750 days.

(21) Appl. No.: 14/598,186

(22) Filed: Jan. 15, 2015

(65) Prior Publication Data

US 2015/0198547 A1    Jul. 16, 2015

(30) Foreign Application Priority Data

Jan. 16, 2014    (SG) .................................. 201400352

(51) Int. Cl.
*G01N 25/72*    (2006.01)
*G01J 5/02*    (2006.01)
*G01J 5/00*    (2006.01)

(52) U.S. Cl.
CPC ............... *G01N 25/72* (2013.01); *G01J 5/02* (2013.01); *G01J 2005/0081* (2013.01)

(58) Field of Classification Search
CPC ..... G01N 25/72; G01J 5/02; G01J 2005/0081
USPC ........................................................ 374/121
See application file for complete search history.

(56) References Cited

U.S. PATENT DOCUMENTS

| 5,834,661 | A | * | 11/1998 | Nonaka | .................. | G01N 25/72 |
| | | | | | | 374/5 |
| 6,516,084 | B2 | | 2/2003 | Shepard | | |
| 7,083,327 | B1 | * | 8/2006 | Shepard | ................. | G01N 25/72 |
| | | | | | | 374/124 |
| 2001/0030987 | A1 | * | 10/2001 | Plotnikov | .............. | G01K 17/00 |
| | | | | | | 374/10 |
| 2005/0002435 | A1 | * | 1/2005 | Hashimoto | ............ | G01N 25/72 |
| | | | | | | 374/43 |
| 2008/0088824 | A1 | * | 4/2008 | McMillan | .............. | G01N 25/72 |
| | | | | | | 356/51 |

(Continued)

OTHER PUBLICATIONS

Song et al, "The Optimization of Volumetric Displacement Can Uniformize the Temperature Distribution of Heated Ham during a Vacuum Cooling Process", Food Science and Technology Research, 20 (1), 43-49, 2014.*

(Continued)

*Primary Examiner* — Lisa Caputo
*Assistant Examiner* — Nathaniel T Woodward
(74) *Attorney, Agent, or Firm* — Womble Bond Dickinson (US) LLP

(57) ABSTRACT

In various embodiments, a system for detecting a defective sample may be provided. The system may include a chamber. The system may further include a pressure reducing mechanism coupled with the chamber. The system may additionally include a detector. The pressure reducing mechanism may be configured to reduce a pressure in the chamber. The detector may be configured to detect information indicating a temperature of the sample. Various embodiments may be capable of detecting water ingress or fluid ingress into the micro cracks or along the designed discontinuities, like bolts and rivets.

20 Claims, 47 Drawing Sheets

(56) References Cited

U.S. PATENT DOCUMENTS

2008/0111078 A1 5/2008 Sun
2008/0224044 A1* 9/2008 SempriMoschnig .. G01N 25/72
　　　　　　　　　　　　　　　　　　　　　　　　　　250/338.1

OTHER PUBLICATIONS

G. Wróbel, et al., "The Application of Transient Thermography for the Thermal Characterisation of Carbon Fibre/Epoxy Composites", Journal of Achievements in Materials and Manufacturing Engineering, vol. 36, No. 1, pp. 49-56, (Sep. 2009).

V. Vavilov, et al., "Some Novel Approaches to Thermal Tomography of CFRP Composites", $10^{th}$ International Conference on Quantitative InfraRed Thermography, Québec, Canada, 8 pp., (Jul. 27-30, 2010).

Christopher J. Janke, et al., "Composite Heat Damage Assessment", Proceedings: Conference on Characterization and NDE of Heat Damage in Graphite Epoxy Composites, NTIAC, 17 pp., (1993).

W. S. Winters, et al., "An Experimental and Theoretical Study of Heat and Mass Transfer during the Venting of Gas from Pressure Vessels", US Department of Energy Publications, Paper 133, 12 pp., (2012).

Xiao-yan Song et al., "The Optimization of Volumetric Displacement Can Uniformize the Temperature Distribuiton of Heated Ham during a Vacuum Cooling Process", (https://www.jstage.jst.go.jp/article/fstr/20/1/20_43/_pdf/-char/en), Food Science and Technology Research, 20(1), 43-49, Apr. 8, 2014.

\* cited by examiner

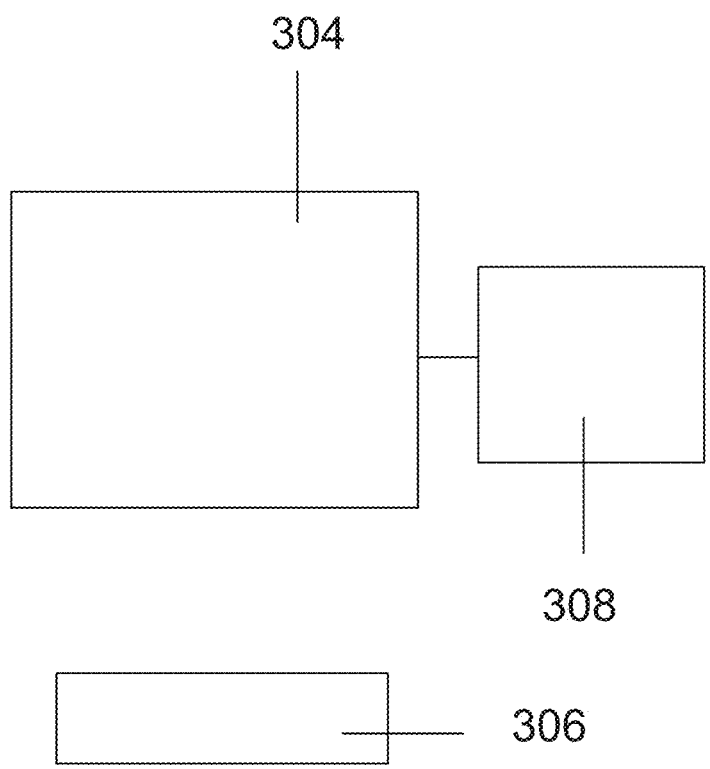

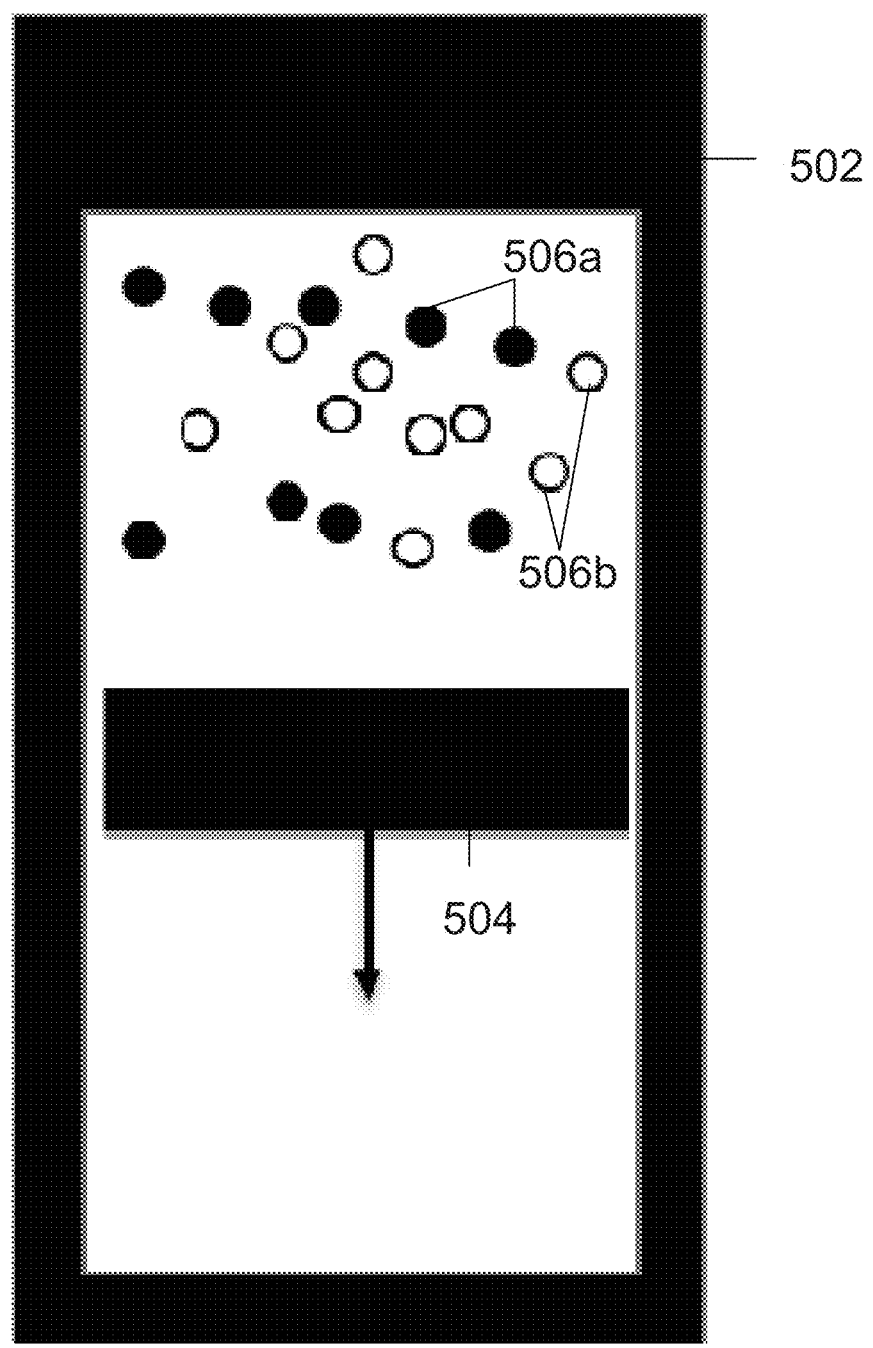

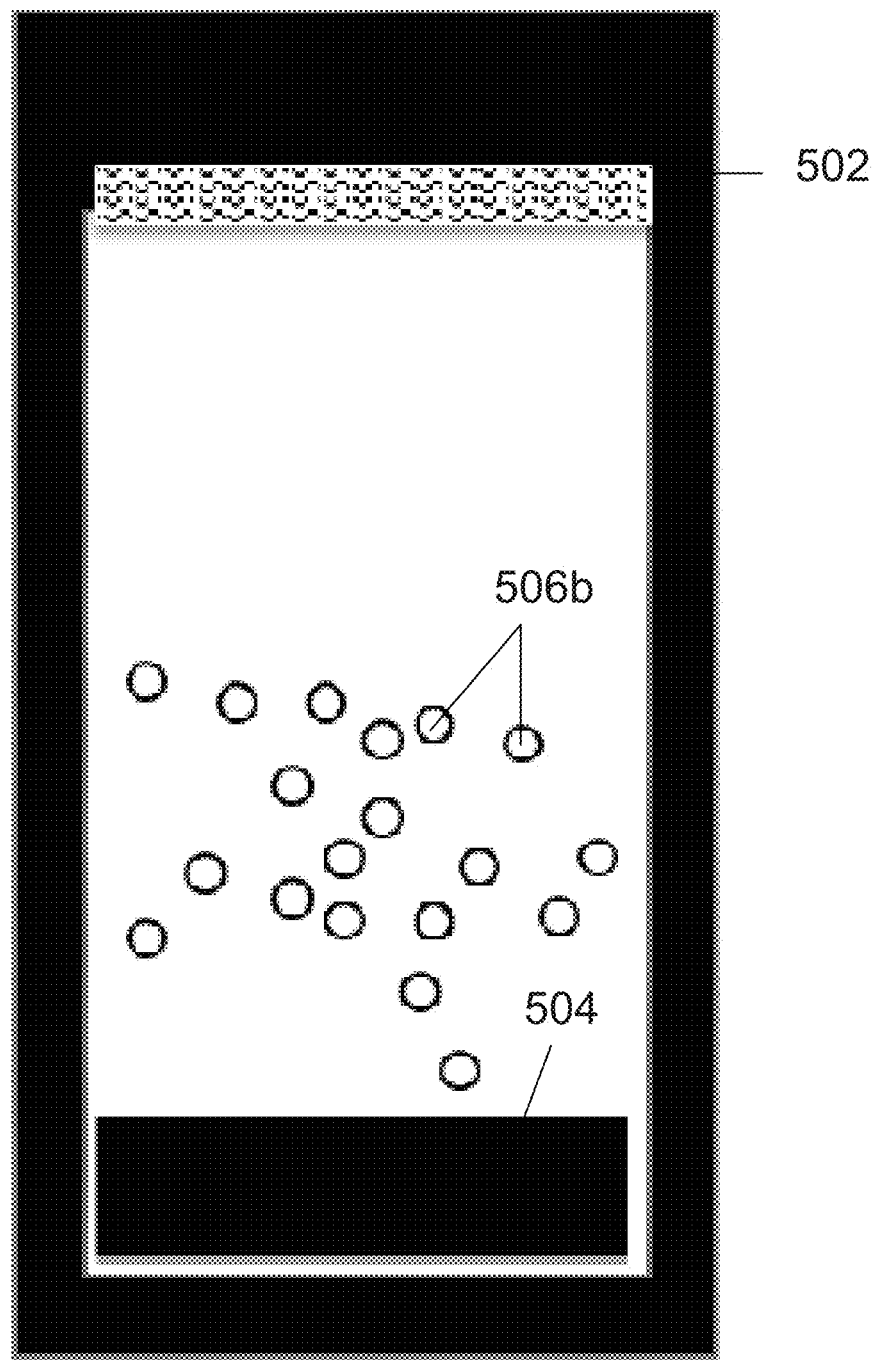

600a

800

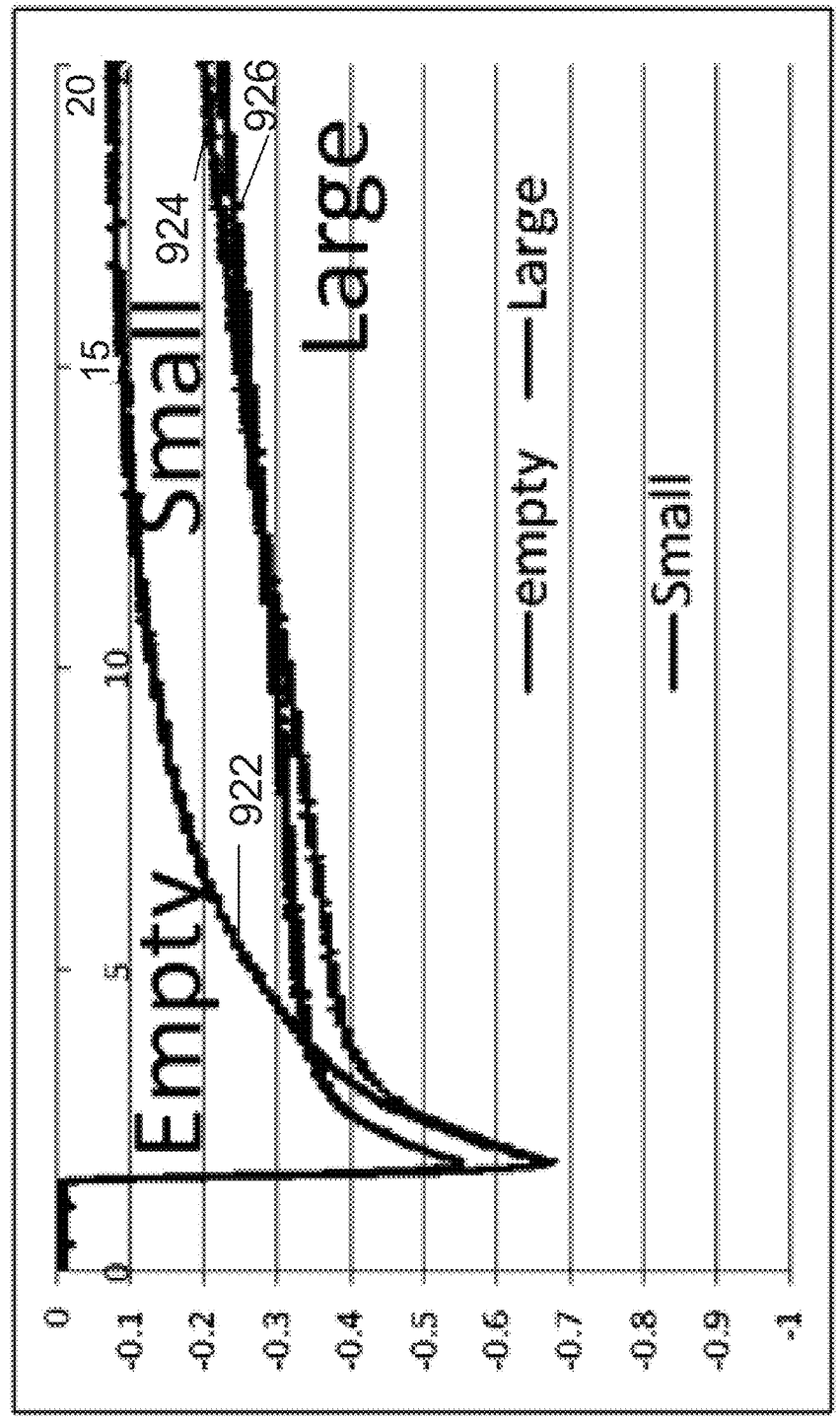

|  | $\rho$, kg/m$^3$ | $c_p$, J/kg*K | $\lambda$, W/m*K | e, W/(m$^2$Ks$^{0.5}$) | $\alpha$, m$^2$/s |
|---|---|---|---|---|---|
| Aluminum | 2700 | 910 | 250 | 2.4*10$^4$ | 1*10$^{-4}$ |
| Tape | 720 | 1336 | 0.05 | 219 | 5.2*10$^{-8}$ |
| Air | 1.18 | 1200 | 0.06 | 9 | 5E-05 |

| # of layers | $\dfrac{\alpha}{(nL)^2}, 1/\sec$ | $K_2/K_1$ | | |
|---|---|---|---|---|
| | | 0.01 sec | 0.1 sec | 1 sec |
| 2 | 2.03 | 7.4E-02 | 2.0E-03 | 4.4E-19 |
| 4 | 0.51 | 1.0E-01 | 4.1E-02 | 4.9E-06 |
| 6 | 0.23 | 1.1E-01 | 7.1E-02 | 1.3E-03 |
| 8 | 0.13 | 1.1E-01 | 8.6E-02 | 9.1E-03 |
| 10 | 0.10 | 1.1E-01 | 9.1E-02 | 1.5E-02 |

| n | 2 | 4 | 6 | 8 | 10 |
|---|---|---|---|---|---|
| $n_{eff}$ | 1.9 | 3.4 | 3.9 | 4.3 | 4.35 |

Reduce a pressure in a chamber

2102

Detect the defective sample by detecting information indicating a temperature of the sample

2104

SYSTEM AND METHOD FOR DETECTING A DEFECTIVE SAMPLE

CROSS-REFERENCE TO RELATED APPLICATION

This application claims the benefit of priority of Singapore application No. 201400352-9 filed Jan. 16, 2014, the contents of it being hereby incorporated by reference in its entirety for all purposes.

TECHNICAL FIELD

Various aspects of this disclosure relate to systems and methods for detecting defective samples.

BACKGROUND

Thermography is an imaging technique based on infrared emission by an object at a particular temperature (grey body radiation). Thermography may include passive thermography or active thermography. Active Thermography is defined as applying a stimulus to a target to cause the target to heat or cool in such a way as to allow characteristics of the target to be observed when viewed by thermal imagery. Active thermography plays a crucial role as a non-destructive technique in many industries, especially in aerospace. Electromagnetic excitation is the most commonly used way of exciting the sample among thermo graphic techniques.

Thermography may also be classified as point imaging thermography, line imaging thermography, area imaging thermography and three-dimensional (3D) imaging thermography (tomography). Area or 3D imaging thermography may also be classified as one-sided or two-sided thermography. Active area imaging thermography may include a detector such as an infrared camera, a heating source as well as image processing software. FIG. 1 is a schematic 100a showing a one-sided optically excited thermography system. A flash lamp 104 is used as a source of electromagnetic radiation to illuminate a surface of sample 102. The infrared camera 106 is used to record the temperature evolution of the sample surface. The source 102 and the detector 106 are arranged on the same side in relation to the sample 104 in one-sided optically excited thermography. The camera 106 and the flash lamp 102 may be coupled to a computer 108. The computer 108 may be configured to acquire data from the camera 106 as well as configured to control the camera 106 and flash lamp 102.

FIG. 2 is a schematic 200a showing a two-sided optically excited thermography system. An infrared radiator or heating lamp 202 is used as a source of electromagnetic radiation to illuminate a sample 204. The infrared camera 206 is arranged at the side (of the sample 204) opposite the radiator 202 to record the temperature evolution. The source 202 and the detector 206 may be arranged on opposite sides in relation to the sample 204 in two-sided optically excited thermography. The camera 206 may be coupled to a computer 208.

The lamp radiator 104, 204 may be a tungsten filament lamp with broad spectral response but in general, alternative sources with spectral components from UV to microwave have been utilized by different groups. This technique has been particularly successful in finding delaminations in Fiber Reinforced Plastics (FRP). The thermo-physical properties of such defects display a high contrast to the fibers and matrix of FRP. Such substantial contrasts allow the lateral conduction in the FRP to be disregarded and heat propagation within the sample be treated as a one dimensional (1D) problem, making it possible to extract depth information from the thermography data. However, for defects with much lower contrast, the effectiveness of active thermography may drop dramatically.

One sided active thermography (shown in FIG. 1) heavily relies on the one-dimensional (1D) approximation of heat diffusion into the semi-infinite sample for processing the acquired data. For the case of semi-infinite solid, the solution may be analytically defined through the dimensional analysis depending on the boundary condition at the surface. For the most common approach, the instantaneous plane Dirac heat source is assumed, which is implemented through application of flash lamps. In this case, the solution for temperature $T(\alpha,z,t,Q')$ for $t>0$ is a function of material diffusivity ($\alpha$) in [m$^2$/s], depth (z) in [m], time (t) in [s], and energy density Q' that the surface was subjected to. Q' may be defined as follows:

$$Q' = Q/\rho c_p A \quad (1)$$

where Q is the energy, $\rho$ is the density of the sample, A is the surface area and $c_p$ is the specific heat capacity of the sample in [J/kgK].

Among all these variables only Q' has unit of temperature in it, i.e.

$$[Q'] = [m]*[K] \text{ (meter-Kelvin)} \quad (2)$$

As other units cannot remove temperature dependence, Q' cannot be used as part of any dimensionless variable of exponential or trigonometric function in the solution. Hence, only $\alpha$, z, and t remain. The only dimensionless combination that can be formed from these parameters is $z/\sqrt{(\alpha t)}$. In order to satisfy the dimensions of temperature the solution should depend on either q/z or $q/\sqrt{(\alpha t)}$. In our case only the second variant makes sense for $t>0$ and $z=0$. Hence, the solution should have a form of $$T = \frac{Q'}{\sqrt{\alpha t}} U(\eta) \quad (3)$$

where $$\eta = \frac{z}{\sqrt{\alpha t}} \quad (4)$$

Looking at partial differentiation by z and t of this function, $$\frac{\partial T}{\partial t} = \frac{dT}{d\eta}\frac{\partial \eta}{\partial t} = -\frac{z}{2t\sqrt{\alpha t}}\frac{dT}{d\eta} \quad (5)$$

$$\frac{\partial T}{\partial z} = \frac{dT}{d\eta}\frac{\partial \eta}{\partial z} = -\frac{1}{\sqrt{\alpha t}}\frac{dT}{d\eta} \quad (6)$$

$$\frac{\partial^2 T}{\partial z^2} = \frac{d}{d\eta}\left(\frac{\partial T}{\partial z}\right)\frac{\partial \eta}{\partial z} = \frac{1}{\alpha t}\frac{d^2 T}{d\eta^2} \quad (7)$$

The implications of these transformation is that the partial differential equations for heat diffusion become an ordinary differential equation as follows:

$$\frac{d^2 T}{d\eta^2} = -2\eta \frac{dT}{d\eta} \quad (8)$$

The implication is that from the projection of temperature evolution at the surface (z=0), one can directly reconstruct the depth distribution at each value of z. Hence, if the measured result deviates form the solution for the semi-infinite body due to the presence of a defect, the time of the onset of deviation may be directly translated into the depth of the defect. However, deviation from 1D model can also happen due to 3D diffusion and the proposed approximation is invalid. For 3D heat diffusion to be ignored one or several of the following criteria should to be satisfied:

1) The surface heating is uniform, so that there are no lateral gradients.

2) The contrast in thermo-physical parameters between defect and sound regions of the sample is high enough to create temperature gradients much larger in comparison with deviation from one dimensional (1D) solution.

3) The detection is performed shortly after the heat source is switched off, so that heat diffusion is minimal. Similarly this criterion can be defined if the location of the defect is close to the surface.

In all other conditions the estimation of z may be grossly inaccurate.

The most common method for heating the surface in active thermography is to use halogen lamps. The illumination with such lamps is inherently non-uniform due to lamp geometry. It is possible to achieve a limited relatively uniform area on the sample surface if 2 or more lamps are implemented simultaneously. However, it dramatically increases the complexity and cost of the system. Due to limited area of uniformity, even for such complex system, the lateral conduction may eventually kick in. At the same time, even if the perfectly uniform illumination can be achieved, it may not guarantee the uniform heat transfer to the surface. Sample and set-up geometry may affect the incidence angle of the light form the lamp, which can have very strong effect on absorption efficiency. Absorption efficiency may also be affected by surface contamination, microstructure or semi-transparency of the top layers. All these effects on absorption efficiency may create localized lateral temperature gradients, which will make the 1D approximation poorly suitable in those locations. These gradients may often disappear in a short period of time if lateral conductivities are high enough. However, at longer periods, the third criterion may not be satisfied. In most cases, active thermography may be implemented when the second criterion is imposed, which means that the contrast in thermo-physical parameters between defect and sample may be much higher than the effects due to 3D diffusion.

The limitations of the conventional active thermography based on flash lamps may be summarized in a following manner:

1) It may be challenging to achieve uniform illumination of the material, which introduces lateral temperature gradients that will dominate the IR image.

2) Even if the uniformity of illumination can be achieved, it may be practically impossible to avoid variation of the light absorption at the surface, which may depend on material composition, surface structure and finishing and presence of surface contamination.

3) Even after the flash is applied, the glow from the lamp may stay strong for several seconds and may be reflected from the sample into the camera. This may not make it possible to use the thermography at early stages of thermal transition.

4) Application in ambient condition may cause cooling of the surface through convection, which may contributes quite a lot after 10 seconds of observation.

All these issues may limit application of active thermography only to the defects with high contrast in thermo-physical parameters in relation to base material under inspection.

SUMMARY

In various embodiments, a system for detecting a defective sample may be provided. The system may include a chamber. The system may further include a pressure reducing mechanism coupled with the chamber. The system may additionally include a detector. The pressure reducing mechanism may be configured to reduce a pressure in the chamber. The detector may be configured to detect information indicating a temperature of the sample.

In various embodiments, a method for detecting a defective sample may be provided. The method may include reducing a pressure in a chamber. The method may include detecting the defective sample by detecting information indicating a temperature of the sample.

BRIEF DESCRIPTION OF THE DRAWINGS

The invention will be better understood with reference to the detailed description when considered in conjunction with the non-limiting examples and the accompanying drawings, in which:

FIG. 3 is a schematic illustrating a system for detecting a defective sample according to various embodiments.

FIG. 5A is a schematic showing a container enclosing a volume of ideal gas in original state at equilibrium.

FIG. 5C is a schematic showing the state of gas after heat exchange between the slow molecules and the wall.

FIG. 9C is a plot of temperature change (kelvins or K) as a function of time (seconds or s) illustrating the temperature behaviors of a normal surface of the plate (no defect), the small defect and the large defect over time when six layers of masking tapes are covered over the plate.

FIG. 12 is a table showing the thermo-physical parameters for aluminum, tape and air.

FIG. 13 is a table illustrating the relationship between these components at 0.01 seconds (sec), 0.1 seconds (sec) and 1 second (sec) after the start of the back-heating process.

FIG. 17 is a table illustrating the values of effective number of layers ($n_{eff}$) and the actual number of layers (n).

FIG. 21 is a schematic illustrating a method for detecting a defective sample according to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized, and structural and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

FIG. 3 is a schematic 300 illustrating a system for detecting a defective sample according to various embodiments. The system may include a chamber 304. The system may further include a pressure reducing mechanism 308 coupled with the chamber 304. The system may additionally include a detector 306. The pressure reducing mechanism 308 may be configured to reduce a pressure in the chamber 304. The detector 306 may be configured to detect information indicating a temperature of the sample.

In other words, a system for detecting a defective sample may be provided. The system may include a chamber 304 with a pressure reducing mechanism 308. Additionally, a detector 306 is used to detect temperature information on sample surface when the pressure in the chamber 304 is reduced.

The defective sample may include a defect.

Figure 1:
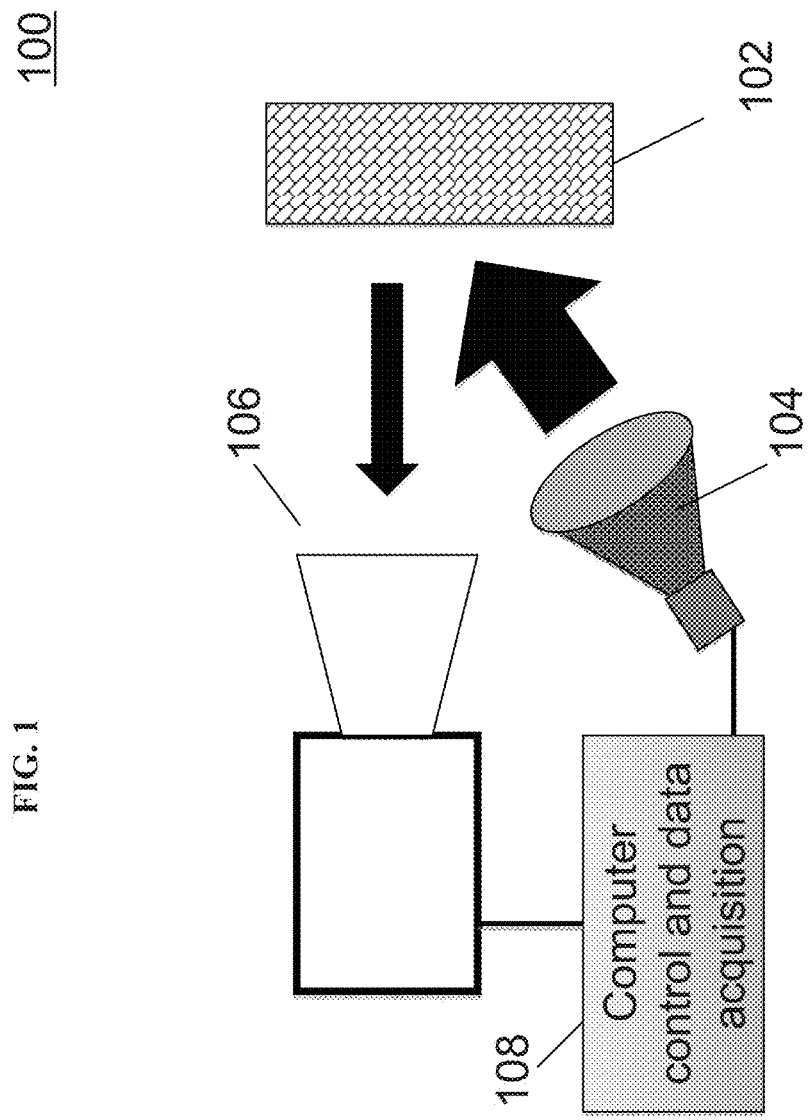
FIG. 1 is a schematic showing a one-sided optically excited thermography system.
Figure 2:
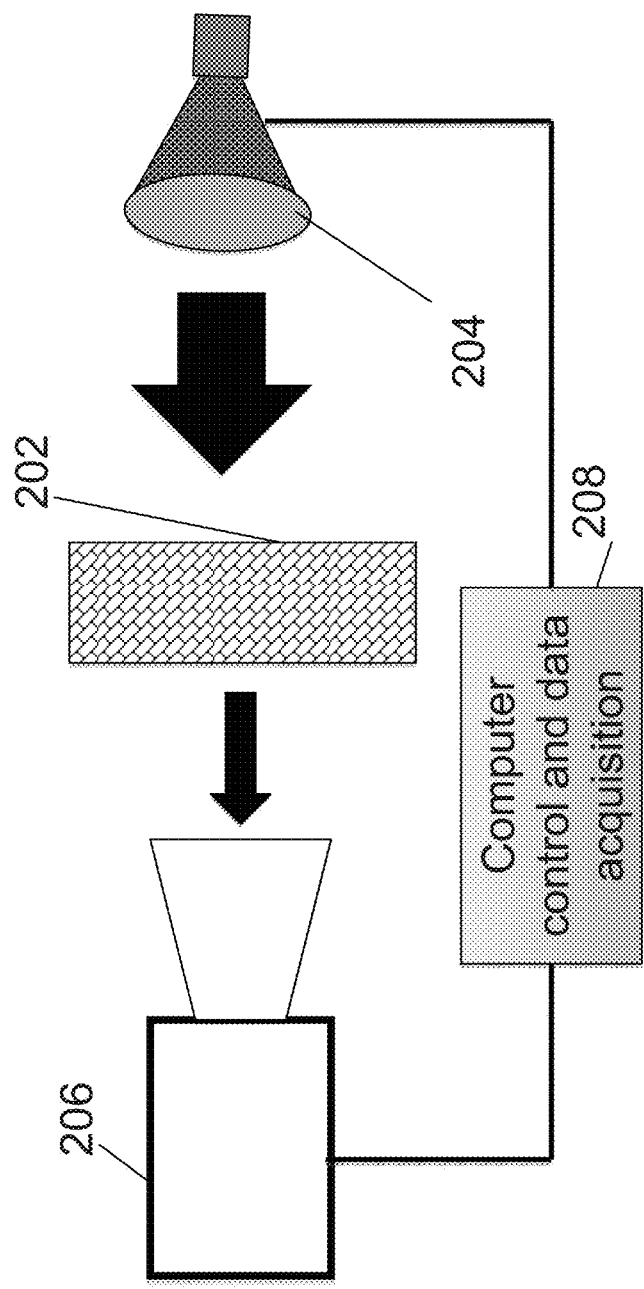
FIG. 2 is a schematic showing a two-sided optically excited thermography system.
Figure 4A:
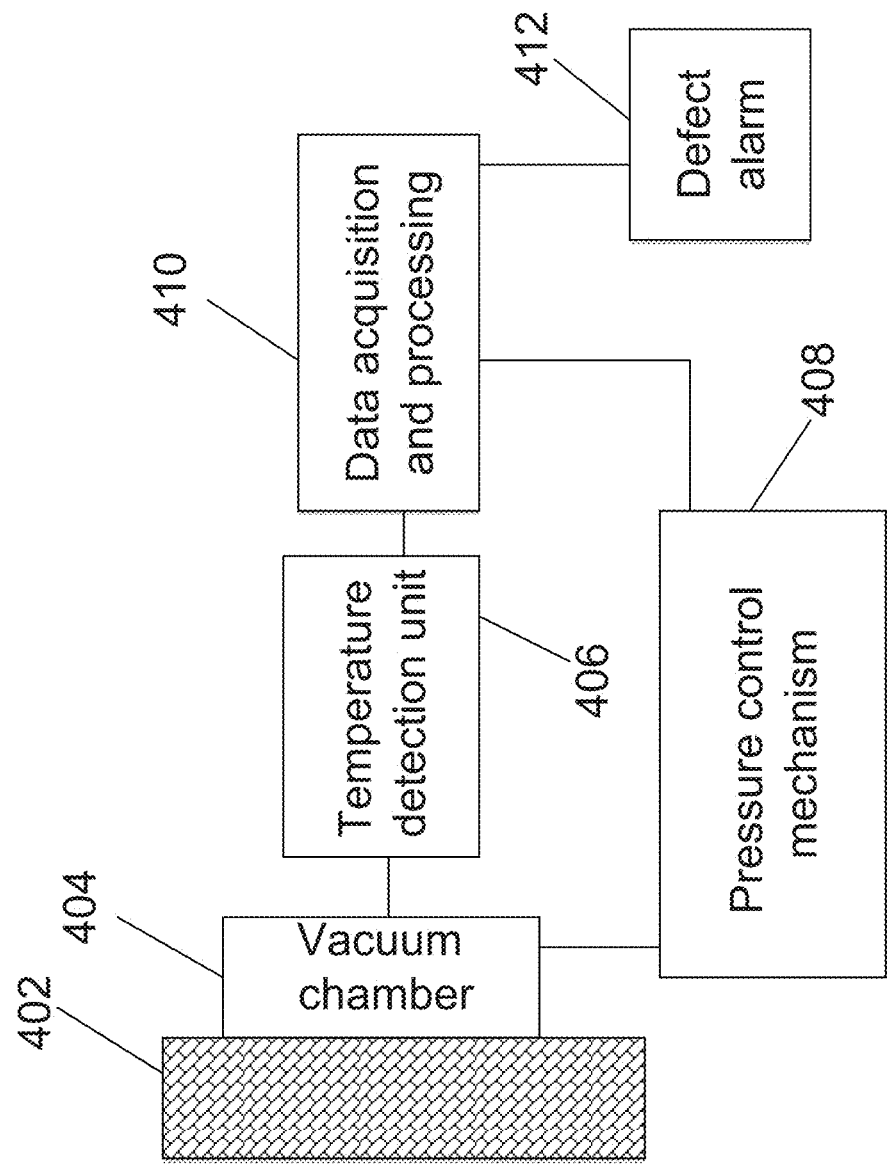
FIG. 4A is a schematic illustrating a system for detecting a defective sample according to various embodiments.

FIG. 4A is a schematic 400a illustrating a system for detecting a defective sample according to various embodiments. The system may use sample 402 as one of the wall of the vacuum chamber 404. The detector 406 may be configured to detect information indicating temperature of the sample surface. The system may further include a pressure control mechanism 408 coupled with the chamber 404. The system may additionally include data acquisition and processing unit 410. This unit may store temperature, pressure and other relevant information, process the data to determine presence of defects and display relevant data. In some embodiments the system may also use alarm unit 412 for informing an operator about the presence of defect.

In other words, a system for detecting a defective sample may be provided. The system may include a chamber 404 with a pressure control mechanism 308. Additionally, a detector 406 is used to detect temperature information on sample surface when the pressure in the chamber 404 is changed. A data acquisition and processing unit 410 may be coupled to the detector 406. A defect alarm 412 may be coupled to the data acquisition and processing unit 410.

The detector 406 may also be referred to as a temperature detection unit.

Figure 4B:
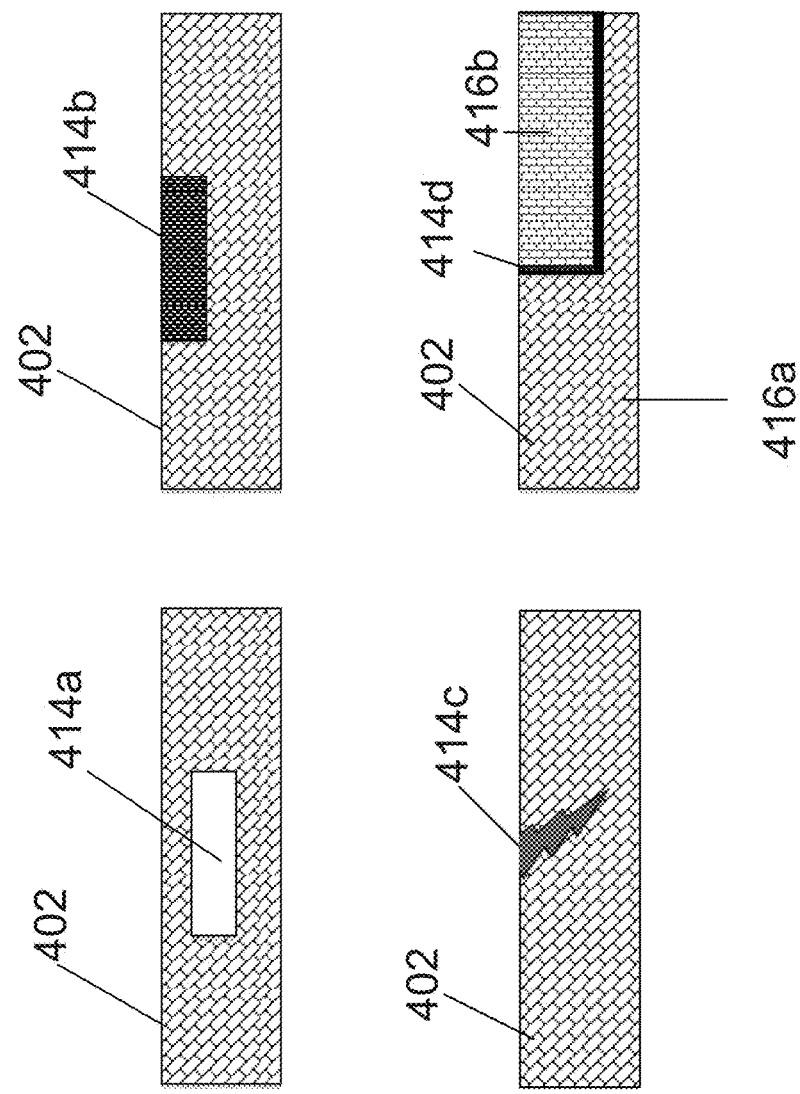
FIG. 4B is a schematic showing possible defects that may be detected by the system according to various embodiments.

FIG. 4B is a schematic 400b showing possible defects that may be detected by the system according to various embodiments. Various embodiments may be suitable for detection of defects 414a under the sample 402 surface. Various embodiments may be suitable for detection of defects 414b on the sample 402 due to material change of the sample 402, such as excessive moisture absorption or over-drying of the sample 402. Various embodiments may be suitable for detection of water or other liquids trapped in the sample 402 due to presence of macro or micro cracks 414c, or other defects, like crevices 414d occurring in otherwise hermetic joints between two materials 416a, 416b.

The temperature drop on dry samples may be due convective transfer of heat from sample to slow molecules inside the 404 chamber after pressure is reduced.

The temperature drop (from the initial temperature to the first temperature) may be due to evaporation of water (or more generally, a fluid) trapped in the sample or on a surface of the sample. Various embodiments may be suitable for detection of moisture ingress in a sample. Various embodiments may be suitable for detection of water or a fluid in a sample.

Various embodiments may seek to address one or more issues as highlighted herein. Various embodiments may be suitable to detect low-contrast defects.

Figure 5B:
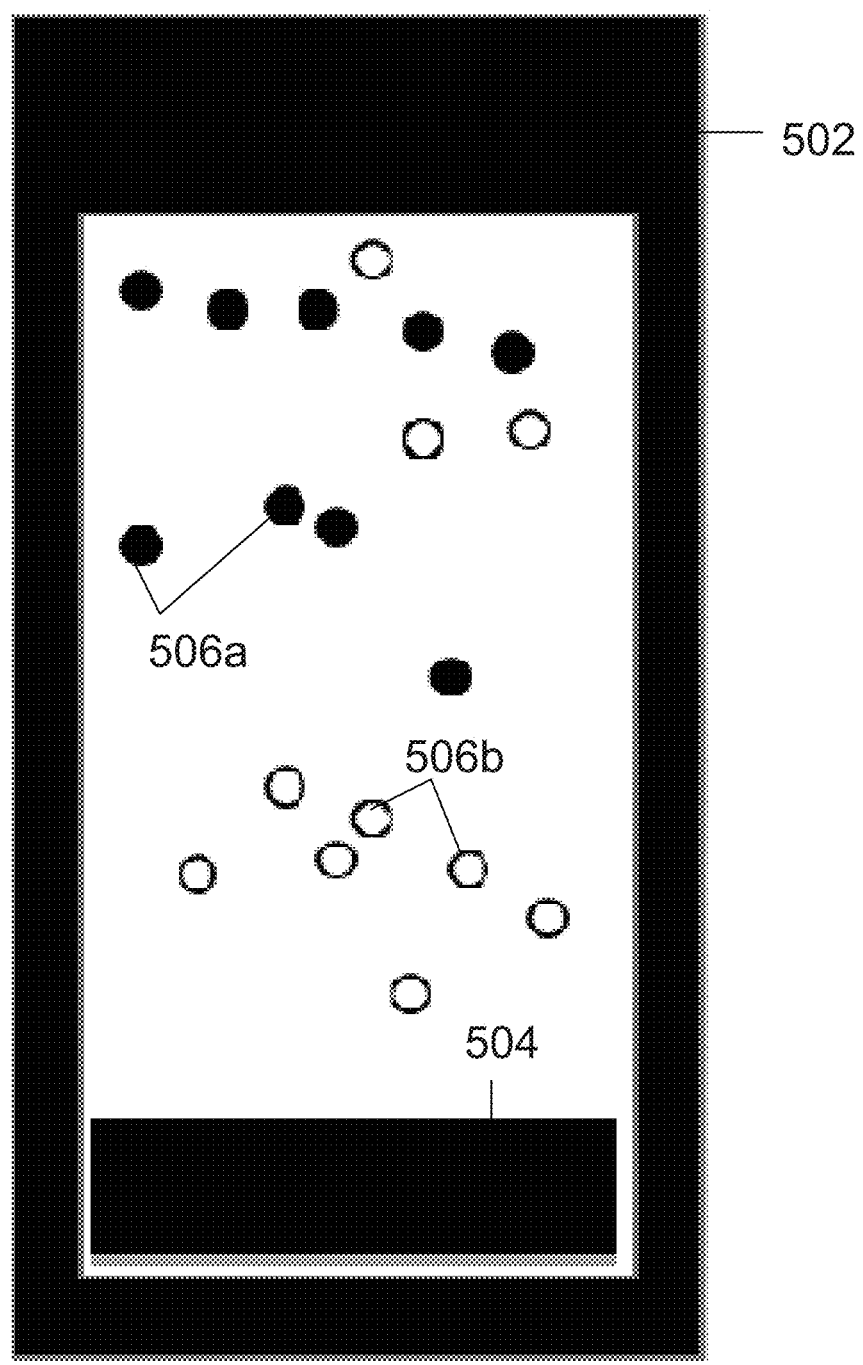
FIG. 5B is a schematic showing the container of gas after instantaneous increase in volume.

FIGS. 5A-C illustrate the relationship between pressure, volume and temperature that explains the phenomenon observed on dry samples. FIG. 5A is a schematic 500a showing a container 502 enclosing a volume of ideal gas in original state at equilibrium. The gas is confined by piston 504 (fixed to wall of container 502 by a stopper) and may include fast gas molecules 506a and slow gas molecules 506b. The gas may be at pressure $P_1$ and may have a volume $V_2$. The gas may be in thermal equilibrium with the walls of the container and may have temperature $T_1$.

According to Maxwell-Boltzmann distribution law, $$f(v) = \sqrt{\frac{2}{\pi}\left(\frac{m}{kT}\right)^3} \, v^2 \exp\left(\frac{-mv^2}{2kT}\right) \quad (9)$$

where T is the temperature related to the most probable speed, m is mass of a molecule, k is the Boltzmann's constant, v is speed, and f(v) is the probability of finding the molecule with the speed.

FIG. 5B is a schematic 500b showing the container 502 of gas after instantaneous increase in volume. FIG. 5C is a schematic 500c showing the state of gas after heat exchange between the slow molecules 506b and the wall.

Figure 5D:
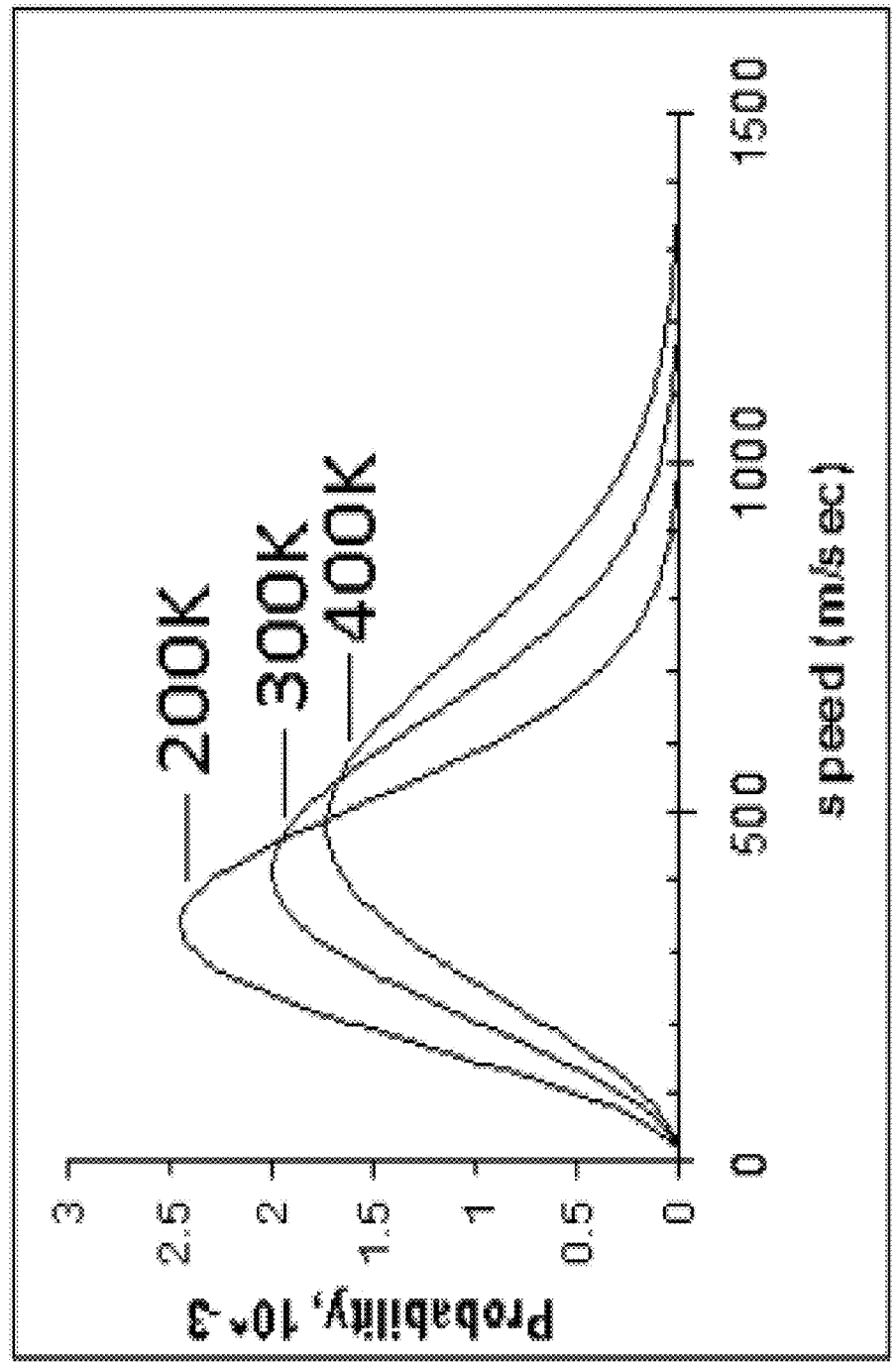
FIG. 5D is a plot of probability against speed (meters/second or m/sec).

FIG. 5D is a plot 500d of probability against speed (meters/second or m/sec). One can see that the distribution at $T_1$ contains a lot of gas molecules with speeds lower (506b) or higher (506a) than speed of molecules actually corresponding to $$T_1 = mv^2/2k \quad (10)$$

If the volume of the containment is increased instantaneously to $V_2$, the molecules with higher speeds 506a may quickly leave the surface that is opposite to the moving wall (FIG. 5B). Hence, only the slow molecules 506b may stay there. Due to temperature difference between the air close to the wall of the container or chamber 502 and these molecules, the heat from the wall may be transferred to the slow molecules 506b. After this transfer, the molecules 506b may gain speed and leave the surface, while at the same time the wall may cool down, as shown in FIG. 5C. If the $V_2 \gg V_1$, it may take a long time for the hot molecules 506a to return to the cooled wall, thus the convective heat transfer at the cold wall may quickly stop. However, the wall may start to heat up due to the conduction heat transfer from the bulk of the wall. This transfer may be solely determined by the thermo-physical properties of this wall and hence, the observation of the back heating may provide information about the wall material or presence of defects inside it.

A similar phenomenon has been recently investigated in details for high pressure vessels. If the gas expanding into the volume with 400 times lower pressure than the surface can cool by up to 100 degrees (Winters et al, "An Experimental and Theoretical Study of Heat and Mass Transfer During the Venting of Gas from Pressure Vessels", US Department of Energy Publications 133, 2012). The experiment shows that for sufficiently high pressure difference, a temperature difference of up to 100 K may be achievable. Temperature may be determined by adiabatic expansion and by heat transfer through walls.

For the case when water or some other fluid is present on the sample surface or is in the sample but can be sucked out to the surface by vacuum the effect can be even stronger. Evaporation is a phase change in the material that is energy intensive. The required energy will be taken from the heat energy of the sample that is in contact with the liquid. This effect has been recently investigated in details for water volumes of several tens of milliliters. The temperature of the surface could drop from room temperature to nearly 0° C. even at slow reduction rates in temperature (Augusto C. M. et al, "Development, calibration and validation of a mathematical model for the low-pressure-vaporization of the water in porous media", International Journal of Heat and Mass Transfer, 73, 574 (2014)). Such temperature changes are easily detectable by any temperature sensor.

In various embodiments, the information may include different temperatures on defective and good samples.

In various embodiments, the information may include different rates of temperature changes from a first temperature to a second temperature.

In various embodiments, the information indicating the temperature may be due to a temperature change from a first temperature to a second temperature, for instance a temperature increase to a second temperature.

For avoidance of doubt, the information indicating the temperature of the sample may include information directly indicating the temperature of the sample or information indirectly indicating the temperature of the sample. In various embodiments, the information indicating the temperature of the sample may be or may include temperature of the sample. In various embodiments, the detector may be or may include a temperature detector.

In various embodiments, the pressure control mechanism 408 may be or may include a pressure reduction mechanism. The information indicating the temperature may be due to a temperature increase from a first temperature to a second temperature. The first temperature may be due to a temperature drop from an initial temperature of the sample due to the reduction in the pressure of the chamber. The second temperature may be an ambient temperature. The first temperature may be due to a temperature drop from an initial temperature of the sample due to the reduction in the pressure in the chamber (due to activating the pressure reduction mechanism). The second temperature may be approximately equal to initial temperature before vacuum condition is initiated. The second temperature may be an ambient temperature. The increase from the first temperature to the ambient temperature may be detected by the detector 306.

The sample 402 may be a wall of the chamber 404 or may be placed inside the chamber 404. The sample may be cooled from the initial temperature to the first temperature upon reduction of pressure within the chamber 402 due to transfer of energy from the sample to the slow molecules of gas within the chamber 404. The sample may then be gradually heated from the first temperature to the second temperature e.g. via conduction from sample bulk.

In various embodiments, the initial temperature of the sample may be equal to the ambient temperature. In various alternate embodiments, the initial temperature of the sample may be more than the ambient temperature.

In various alternate embodiments, the pressure control mechanism 408 may be or may include a pressure increasing mechanism coupled with the chamber. The pressure increasing mechanism may be configured to increase a pressure in the chamber. The information indicating the temperature may be due to a temperature decrease from a first temperature to a second temperature. The second temperature may be lower than the first temperature. The first temperature is due to a temperature increase from an initial temperature of the sample due to an increase in the pressure in the chamber (as a resulting of activating the pressure increase mechanism).

The pressure control mechanism 408 may include a further chamber coupled to the chamber 404. The pressure control mechanism 408 may include a further pressure reducing mechanism coupled to the further chamber. The further chamber may be larger than the chamber 404.

The further chamber may be about ten times larger than the chamber 404. The further chamber may be constantly kept at vacuum or near vacuum by the further pressure reducing mechanism. The further pressure reducing mechanism may be configured to reduce the further pressure in the further chamber to be lower than the pressure in the chamber 404.

The reduction of the pressure in the chamber 404 may be caused by exposure of the pressure in the chamber 404 to the further pressure in the further chamber.

The system may further include a valve mechanism. The further chamber may be coupled to the chamber 404 such that or so that the valve mechanism is between the further chamber and the chamber 404.

The valve mechanism may be configured to be switched between a first position and a second position such that or so that the switching of the valve mechanism from the first position and the second position causes exposure of the pressure in the chamber 404 to the further pressure in the further chamber.

The valve mechanism may include a valve such as an electrically controlled valve. The valve may be a mechanical valve or a pneumatic valve. The chamber may be configured such that or so that the pressure in the chamber is increased prior to exposure of the pressure in the chamber 404 to the further pressure in the further chamber.

The further chamber may include a liquid separator. The further pressure reducing mechanism may include or may be a vacuum pump.

The defective sample may be detected by comparing the information indicating the temperature of the defective sample with further information indicating a temperature of a non-defective sample. A defective region in the defective sample may be detected by detecting a differential rate of increase in temperature between the defective region and a non-defective region.

The chamber 404 may include a gas or may be configured to hold a gas. The gas may be selected from any one of a chlorofluorocarbon gas, a hydrofluorocarbon gas, a hydrochlorofluorocarbon gas, a carbon dioxide gas, a methyl chloride gas and an ammonia gas. The gas may be configured to reduce the temperature of the sample from an initial temperature to the first temperature. The detector 406 may be configured to detect the information indicating the temperature by detecting electromagnetic radiation emitted by the sample. The electromagnetic radiation may be transmitted through at least a portion of a volume enclosed by the chamber 404.

The detector 406 may be configured to detect information indicating a temperature of the sample via any suitable means. For instance, the detector may be a contact-based sensor (e.g. a thermocouple) configured to detect the information indicating the temperature by contacting the sample or the detector may be configured to detect the information indicating the temperature by detecting electromagnetic radiation emitted by the sample.

Figure 6A:
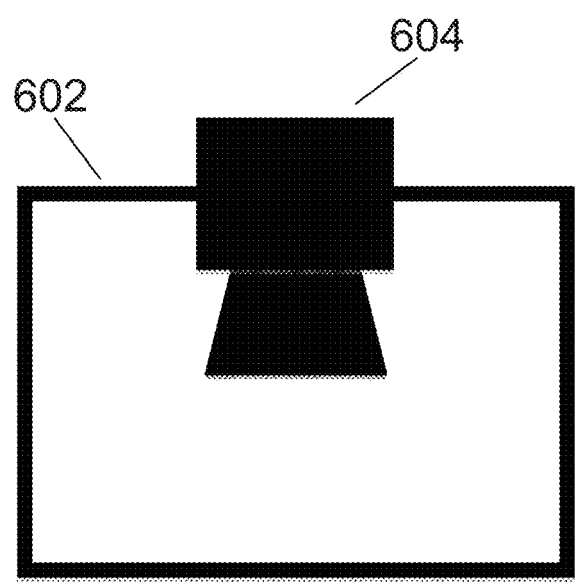
FIG. 6A is a schematic of a chamber in which a detector (based on detection of electromagnetic radiation) is attached to the wall of the chamber according to various embodiments.
Figure 6B:
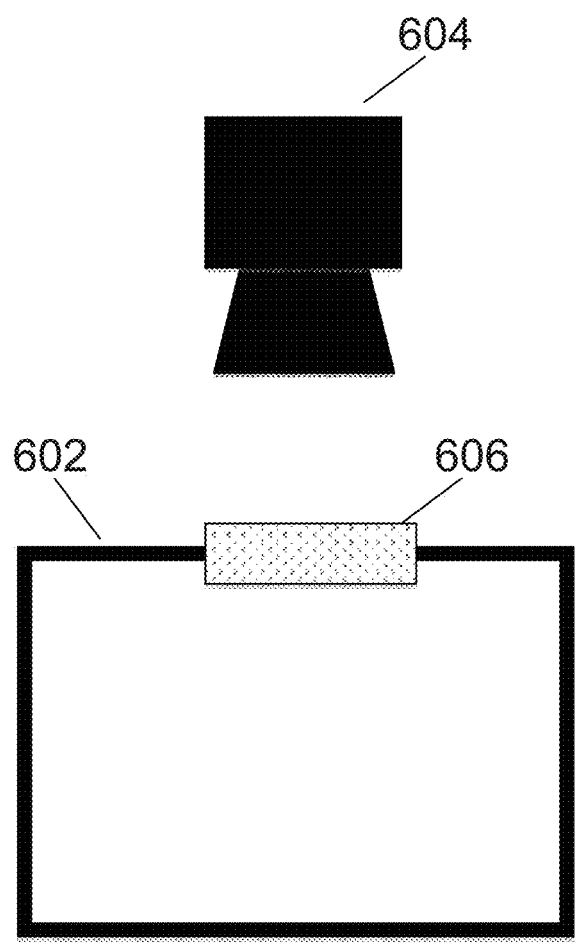
FIG. 6B is a schematic of a chamber with or including a window (in one of the walls) according to various embodiments.

FIG. 6A is a schematic 600a of a chamber 602 in which a detector 604 (based on detection of electromagnetic radiation) is attached to the wall of the chamber 602 according to various embodiments. FIG. 6B is a schematic 600b of a chamber with or including a window 606 (in one of the walls) according to various embodiments. The window 606 may be configured to allow electromagnetic radiation emitted by the sample to the detector 604 (placed outside of the chamber 602). The window 606 may further include an antireflection coating on the window. The coating may be configured to allow electromagnetic radiation (the electromagnetic radiation matching a spectral range of the detector 604) to the detector 604. The window may be selected from a group consisting of a silicon window, a zinc selenide window and a germanium window. The electromagnetic radiation may be infrared radiation.

Figure 6C:
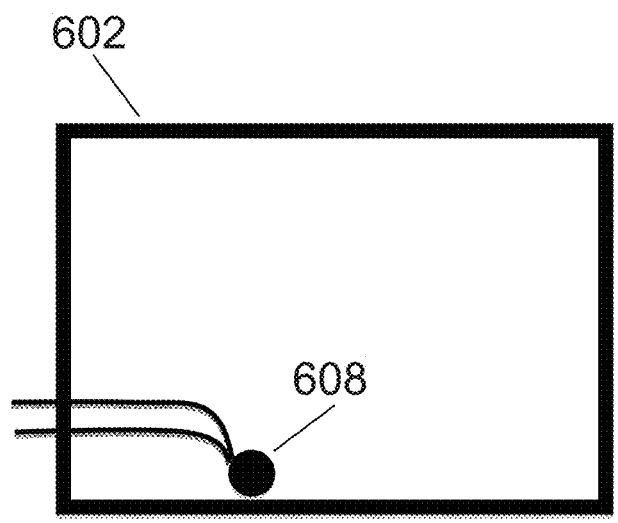
FIG. 6C is a schematic of a chamber where conduction based temperature sensor or set of sensors is used for temperature detection according to various embodiments.

The detector 604 may instead be based on photoelectric detectors, photothermal detectors or detectors based on other suitable principles. The detector maybe be cooled or uncooled detectors FIG. 6C is a schematic 600c of a chamber 602 where conduction based temperature sensor or set of sensors 608 is used for temperature detection according to various embodiments. The conduction based sensor may be in contact with the sample. The sensor may be a thermocouple, thermistor or other contact based sensor.

In various embodiments, the chamber 602 may be an enclosed chamber and the sample is adhered to or attached to or received by a wall of the chamber 502. In various embodiments, the chamber 602 may be initially open (i.e. the chamber may be an open cavity) and may form an enclosed chamber when the sample is received by or adhered to the chamber 602. The chamber 602 may include an open chamber. In various embodiments, the system may include an open cavity to receive or to adhere to the sample (e.g. via vacuum suction) so that the cavity and the sample form an enclosed chamber 602.

The information indicating the temperature may be due to a temperature increase from a first temperature to a second temperature. The second temperature may be higher than the first temperature. The first temperature may be due to a temperature drop from an initial temperature of the sample due to the reduction in the pressure in the chamber 602. The temperature drop may be due to evaporation of water or fluid in the defective sample. The temperature drop may be due to evaporation of water in the defective sample. The second temperature may be an ambient temperature.

The system may further include a vacuum chuck. The vacuum chuck may be configured to hold the chamber 602 to the sample or may be configured to hold the sample to the holder. The vacuum chuck may be configured to hold the chamber 602 to the sample such that a surface of the sample is cooled by the reduction in the pressure of the chamber.

The system may further include pressure sensor (s) for precise control and data logging of pressure and pressure reduction rate. The pressure sensor may be coupled to the chamber 602. The pressure sensor and/or the detector 604 may be coupled to a data-recording unit.

The system may further include may further include specific gas sensing devices for outgassing or evaporating materials constituting the defect.

Figure 7A:
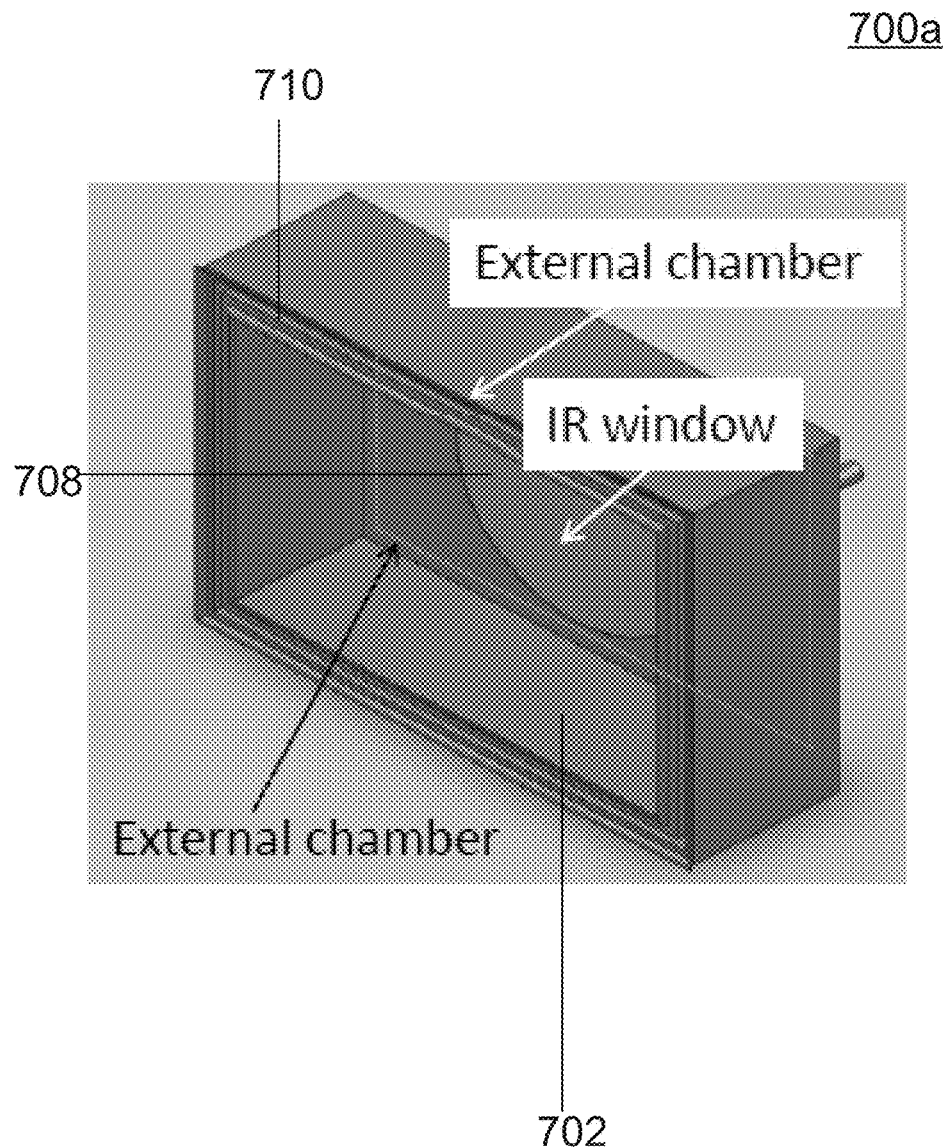
FIG. 7A is a schematic of a perspective view of a chamber according to various embodiments with infrared (IR) window and vacuum chuck.
Figure 7B:
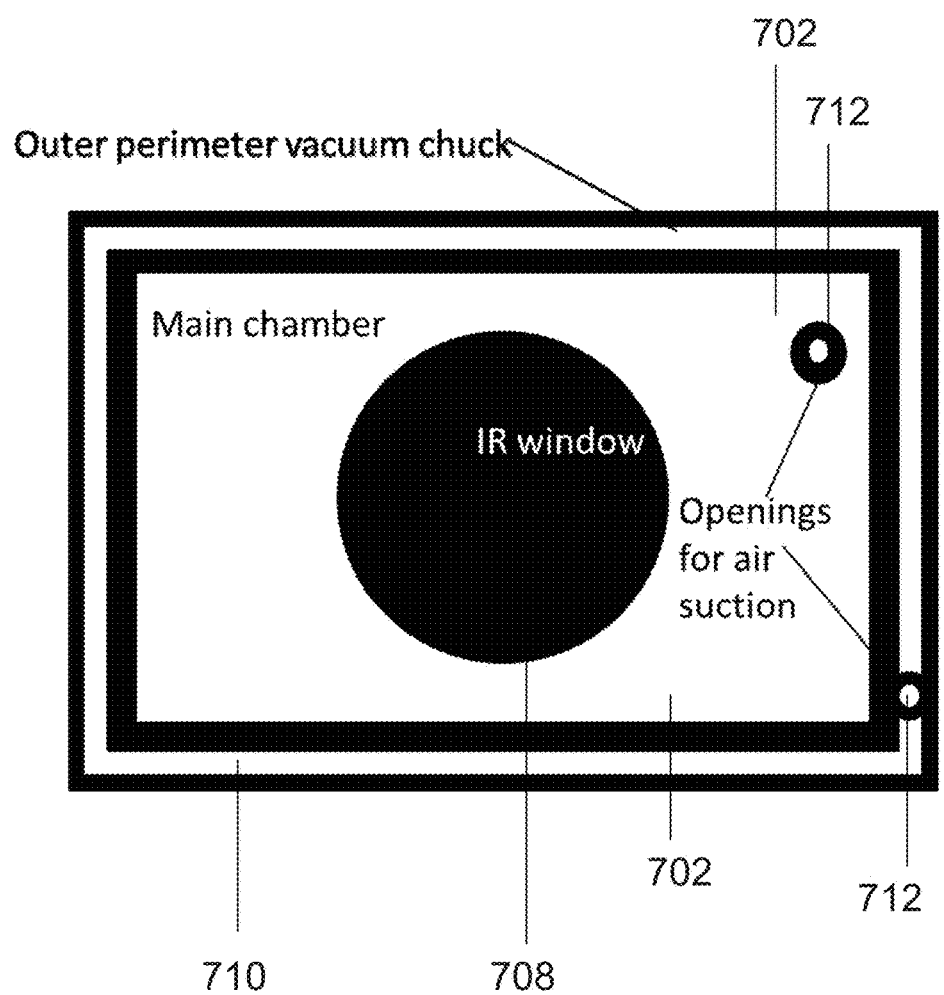
FIG. 7B is a schematic of a front view of the chamber shown in FIG. 7A according to various embodiments.
Figure 7C:
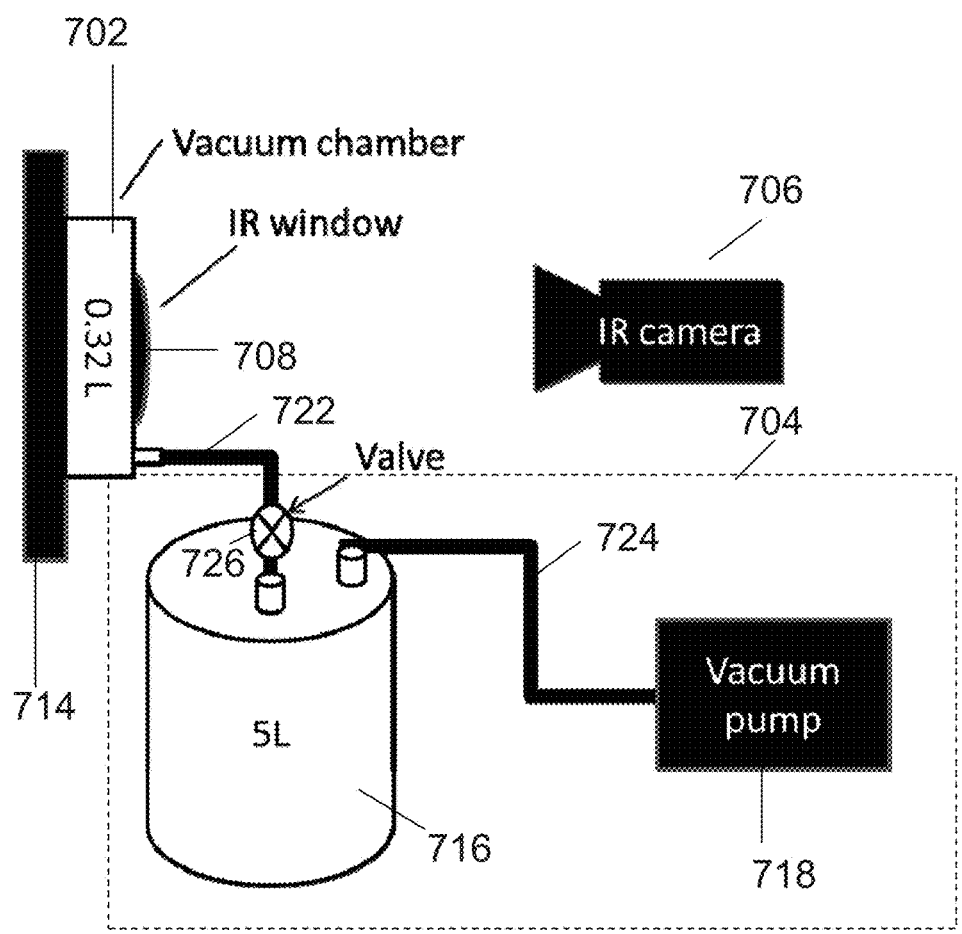
FIG. 7C is a schematic of a system for detecting a defective sample according to various embodiments.

FIG. 7A is a schematic 700a of a perspective view of a chamber 702 according to various embodiments with infrared (IR) window 708 and vacuum chuck 710. FIG. 7B is a schematic 700b of a front view of the chamber 702 shown in FIG. 7A. FIG. 7C is a schematic 700c of a system for detecting a defect in a sample according to various embodiments. The system may include a chamber such as the chamber 702 illustrated in FIGS. 7A-B. The chamber 702 may include an infrared window 708 (IR window). The infrared window 708 (IR window) may be configured to allow electromagnetic radiation such as infrared radiation to transmit or pass through. The infrared window 708 may be configured to allow electromagnetic radiation emitted by the sample 714 to the detector 706 e.g. an infrared (IR) camera.

The system may also include a pressure reducing mechanism 704 coupled with or coupled to the chamber 702. The system may additionally include a detector 806. The pressure reducing mechanism 704 may be configured to reduce a pressure in the chamber 702. The detector 706 may be configured to detect information indicating a temperature of the sample 714.

The system may further include an external chamber 710. The external chamber may be around the perimeter of the chamber 702 and may be referred to as an outer perimeter vacuum chuck. The external chamber 710 may be configured to be attached to the sample 714 via vacuum suction (e.g. via openings 712 shown in FIG. 7B). The sample 714 may be attached to the chamber 702 via the external chamber 710. The external chamber 710 may provide a firm attachment to the sample surface to confine evacuated area. The external chamber 710 may be coupled to a separate, dedicated external chamber vacuum pump (not shown in FIGS. 7A-C). In other words, the vacuum chuck 710 on the outer perimeter may be designed for the purpose of securing the chamber 702 to surfaces placed at arbitrary angle including ceiling (i.e. sample 714). The chuck 714 may create vacuum that is designed to hold up to 70 kg of weight. This chuck 714 may be evacuated by a separate pump from the one used to evacuate the main chamber 702. The chamber 702 may be an open chamber and may become an enclosed chamber when the sample is attached to the chamber 702, for instance via vacuum suction through the external chamber 710. The sample may become a wall of the enclosed chamber 702.

Vacuum may be created within chamber 702 (which may also be referred to as the internal chamber) through pressure reducing mechanism 704. The vacuum created may (instantaneously) cool the surface of the sample 714. The pressure reducing mechanism 704 may include a further chamber 716 (such as a liquid separator) coupled to the chamber 702. The pressure reducing mechanism may additionally include a further pressure reducing mechanism 718 (e.g. a (main) vacuum pump separate from the external chamber vacuum pump) coupled to the further chamber 716. The chamber 702 and the further chamber 716 may be coupled via a coupling means 722 such as a hose or a channel. The (main) vacuum pump 718 may be coupled to the further chamber 716 via a further coupling means 724 such as a further hose or a further channel.

The main chamber 702 may be built to have a relatively small volume in order to allow faster evacuation and thus more instantiations transition. This chamber 802 may not be directly connected to the vacuum pump 718. Instead, a volume of 5 liters (or other amount) of liquid separator may be placed in between in order to achieve larger and more repeatable pressure difference.

The IR window 708 may allow observation of transient behavior at evacuated surface. In other words, the IR window 708 (e.g. a silicon window) in the outer wall of the main chamber 702 may allow the IR radiation from the sample 714 to reach the IR camera 706. Placing camera 706 or just objective of the camera 706 into the main chamber may lead to possible damage to the camera 706 and may require a restrictively complicated design. In other words, the detector 706 may be positioned outside the chamber 702.

The sample 714 may be cooled from an initial temperature to a first temperature due to reduction in pressure in the chamber 702. A surface of the sample may form a wall of the chamber 702 so that a volume (of gas) is enclosed by the chamber 702 and the sample 714. The pressure in the chamber 702 may be referred to as the pressure of the volume (of gas) enclosed by the chamber 702 and the sample 714. The reduction of pressure in the chamber 702 may be caused by the pressure reducing mechanism 704. After cooling of the sample 714 from the initial temperature to the first temperature, the first temperature of the sample may increase to a second temperature. The second temperature may be an ambient temperature (of the environment in which the system is positioned in such as the temperature of the room in which the system is arranged in). The detector 706 may be configured to detect information indicating the temperature increase due to a temperature increase from a first temperature to a second temperature. The initial temperature may be substantially equal to the ambient temperature or may be the ambient temperature.

The system may further include a valve mechanism 726 such as a valve. The further chamber 716 may be coupled to the chamber 702 such that the valve mechanism is between the further chamber 716 and the chamber 702. The valve mechanism may be configured to be switched between a first position (closed position) and a second position (open position) such that the switching of the valve mechanism from the first position to the second position causes the exposure of the pressure in the chamber 702 to the further pressure in the further chamber 716. The further pressure may be at a lower pressure than the pressure. As such, when the pressure is exposed to the further pressure, the pressure within chamber 702 is reduced, causing a reduction in temperature from the initial temperature to the first temperature. In other words, when the valve mechanism 726 is switched to an open position, the volume within the main chamber 702 may be exposed to or may be connected to the volume in the further chamber 716, which is at a lower pressure. When the valve mechanism 726 is in a closed position, the volume within the main chamber 702 may be separated or may be isolated from the volume within the further chamber 716. When the valve mechanism 726 is switched from the closed position to the open position, the gas molecules contained in the volume in the chamber 802 is exposed to the volume in further chamber 716. The more energetic molecules may move to the volume in the further chamber, leading to the lower pressure.

Figure 8:
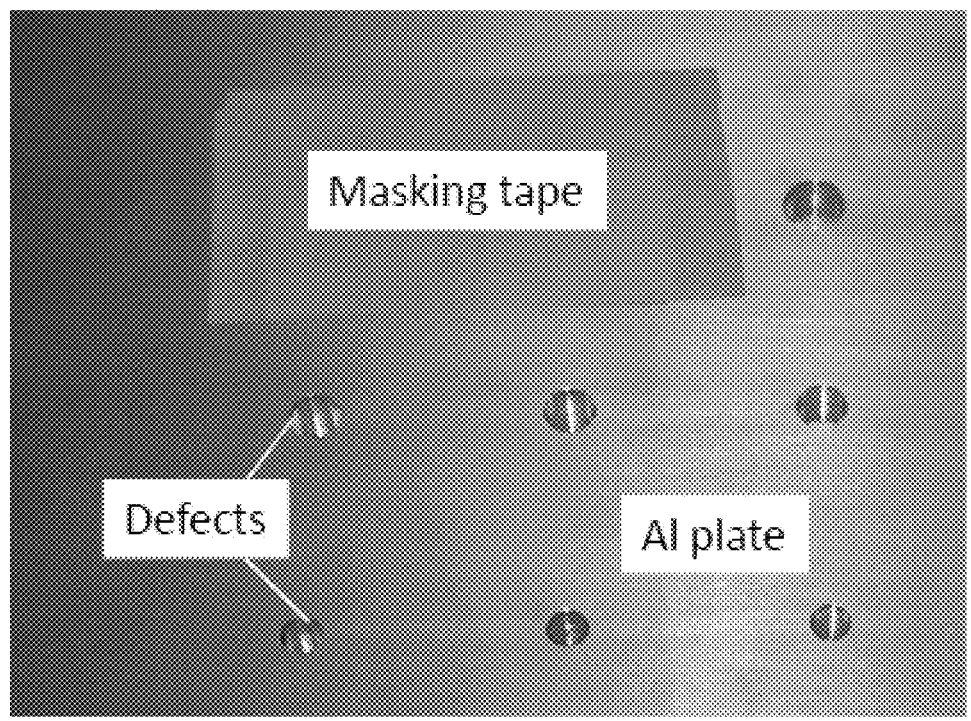
FIG. 8 is an image showing an aluminum plate with holes of different sizes and depths.

For demonstration purposes, a special sample was designed by drilling a large not-through hole and a small not-through hole in an aluminum plate. The large hole may represent a large defect and the small not-through hole may represent a small defect. Then these holes and a normal surface were covered with masking tape of low thermal conductivity. FIG. 8 is an image 800 showing an aluminum plate with holes of different sizes and depths. The holes may be not-through holes. The holes may represent defects in a sample. The open part of the holes may be covered by multiple layers of masking tape.

Figure 9A:
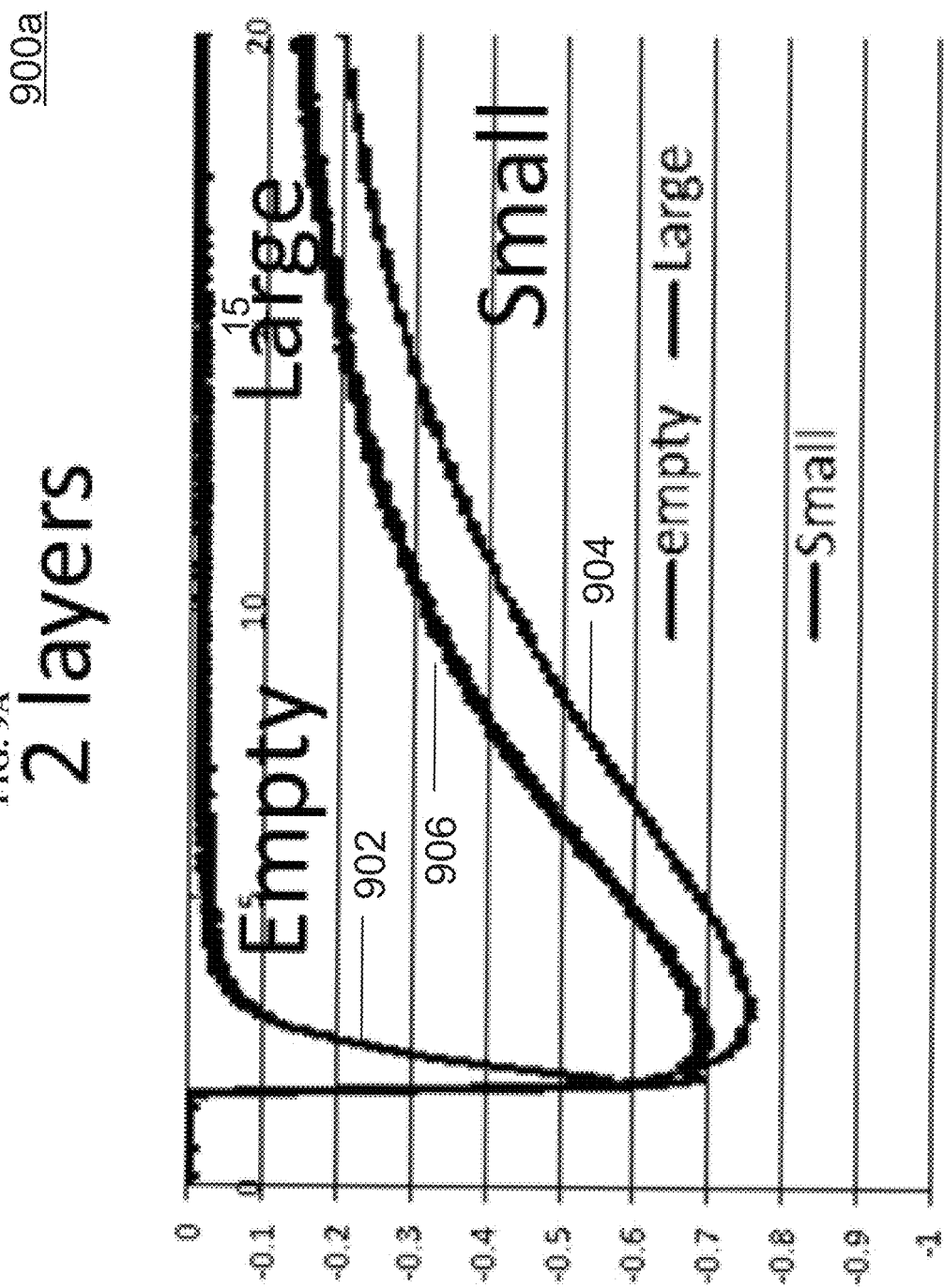
FIG. 9A is a plot of temperature change (kelvins or K) as a function of time (seconds or s) illustrating the temperature behaviors of a normal surface of the plate (no defect), the small defect and the large defect over time when two layers of masking tapes are covered over the plate.
Figure 9B:
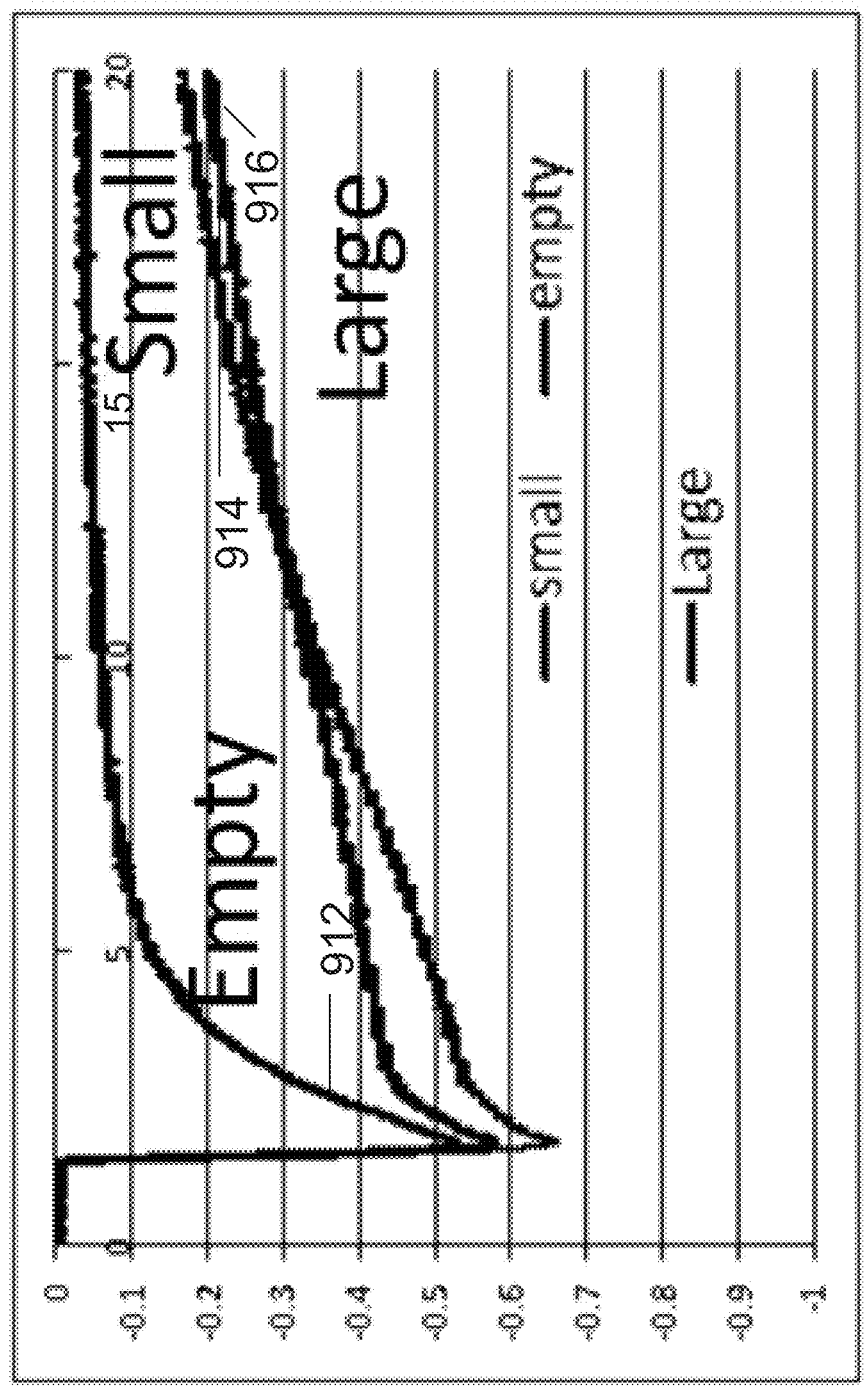
FIG. 9B is a plot of temperature change (kelvins or K) as a function of time (seconds or s) illustrating the temperature behaviors of a normal surface of the plate (no defect), the small defect and the large defect over time when four layers of masking tapes are covered over the plate.
Figure 9D:
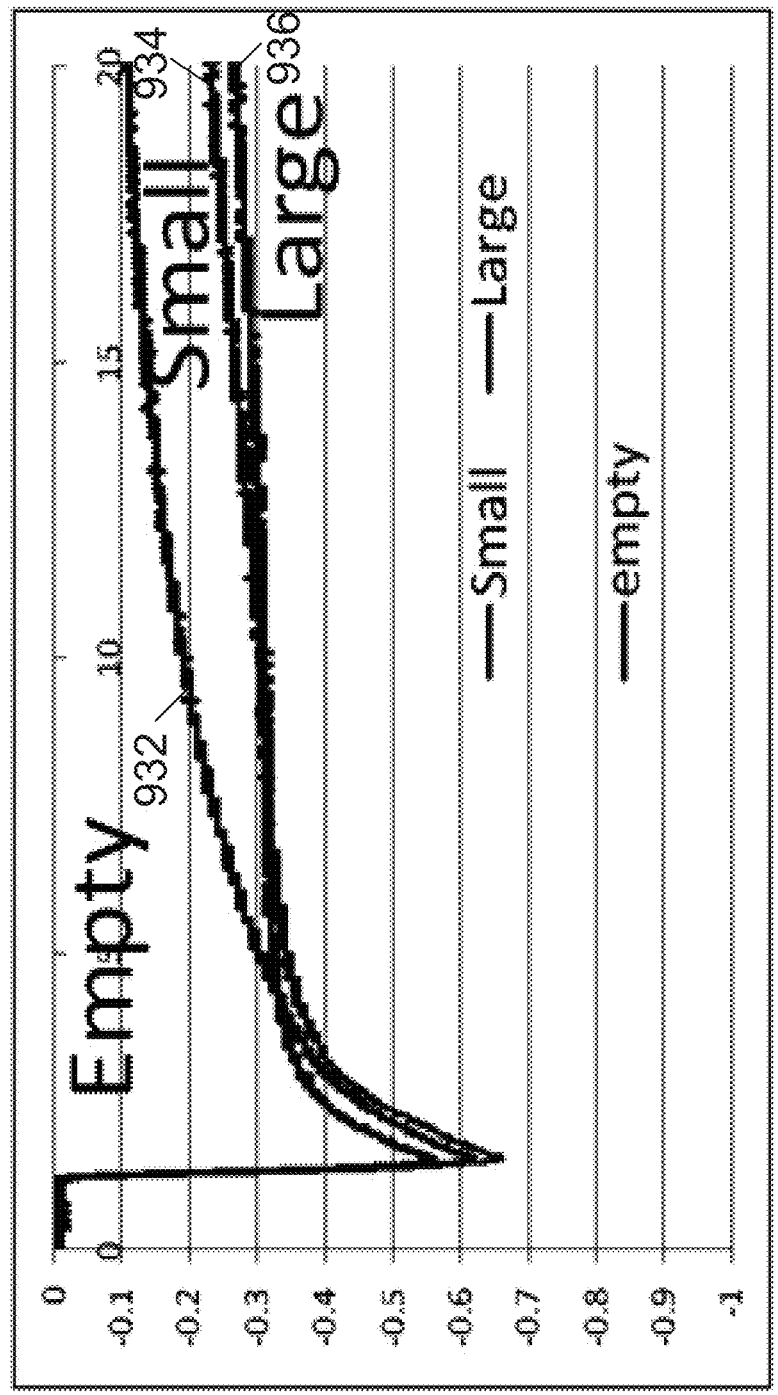
FIG. 9D is a plot of temperature change (kelvins or K) as a function of time (seconds or s) illustrating the temperature behaviors of a normal surface of the plate (no defect), the small defect and the large defect over time when eight layers of masking tapes are covered over the plate.
Figure 9E:
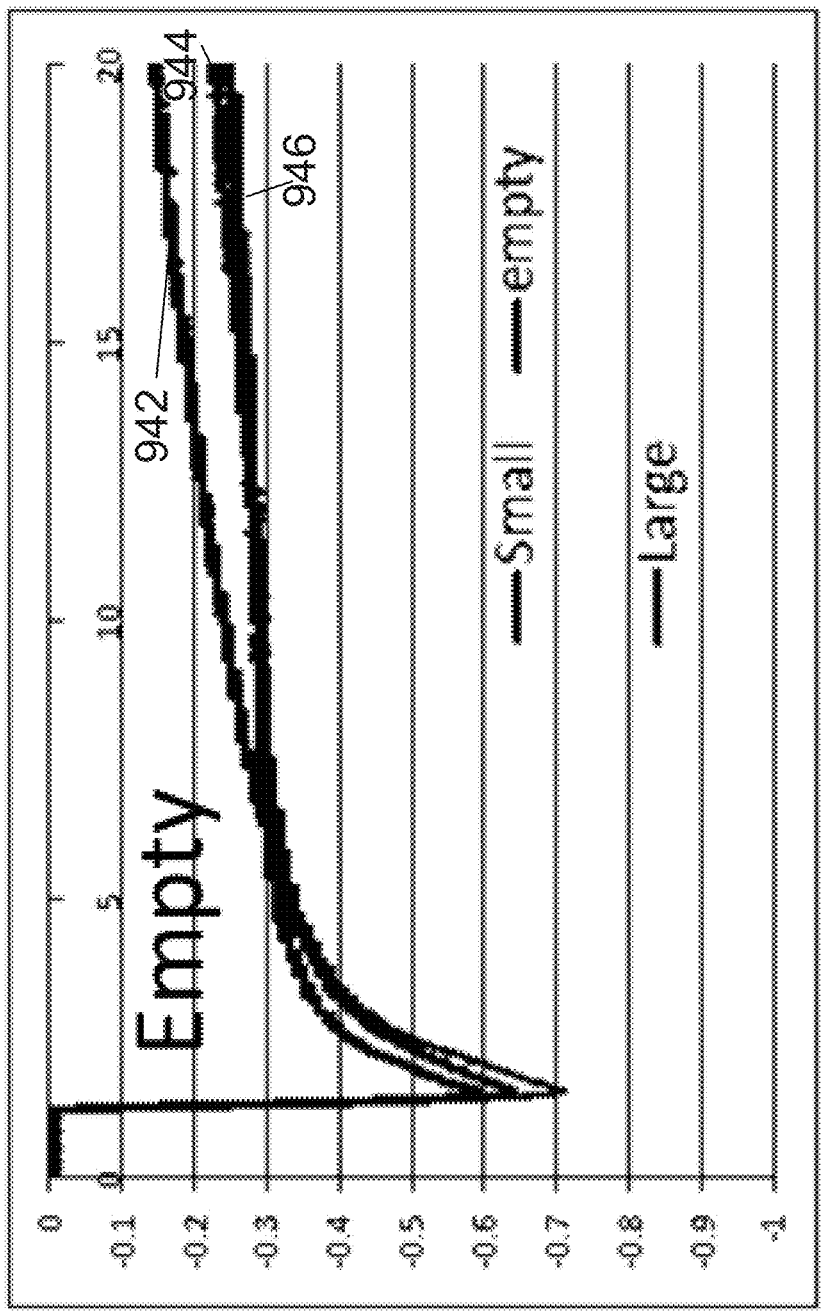
FIG. 9E is a plot of temperature change (kelvins or K) as a function of time (seconds or s) illustrating the temperature behaviors of a normal surface of the plate (no defect), the small defect and the large defect over time when ten layers of masking tapes are covered over the plate.

FIGS. 9A-E illustrate five measurements recorded for different numbers of masking tape layers. Within the presented field of view there are two defects under the tape with lateral dimensions diameters. FIG. 9A is a plot 900a of temperature change (K) as a function of time (s) illustrating the temperature behaviors of a normal surface of the plate (no defect, 902), the small defect (904) and the large defect (906) over time when two layers of masking tapes are covered over the plate. FIG. 9B is a plot 900b of temperature change (K) as a function of time (s) illustrating the temperature behaviors of a normal surface of the plate (no defect, 912), the small defect (914) and the large defect (916) over time when four layers of masking tapes are covered over the plate. FIG. 9C is a plot 900c of temperature change (K) as a function of time (s) illustrating the temperature behaviors of a normal surface of the plate (no defect, 922), the small defect (924) and the large defect (926) over time when six layers of masking tapes are covered over the plate. FIG. 9D is a plot 900d of temperature change (K) as a function of time (s) illustrating the temperature behaviors of a normal surface of the plate (no defect, 932), the small defect (934) and the large defect (936) over time when eight layers of masking tapes are covered over the plate. FIG. 9E is a plot 900e of temperature change (K) as a function of time (s) illustrating the temperature behaviors of a normal surface of the plate (no defect, 942), the small defect (944) and the large defect (946) over time when ten layers of masking tapes are covered over the plate.

Figure 9F:
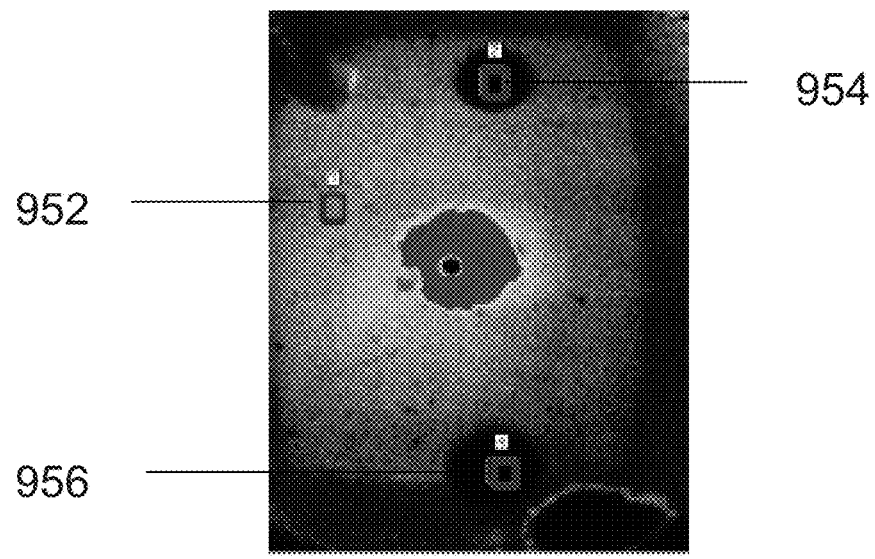
FIG. 9F is an infrared (IR) image of the sample with two layers of tape on the sample.
Figure 9G:
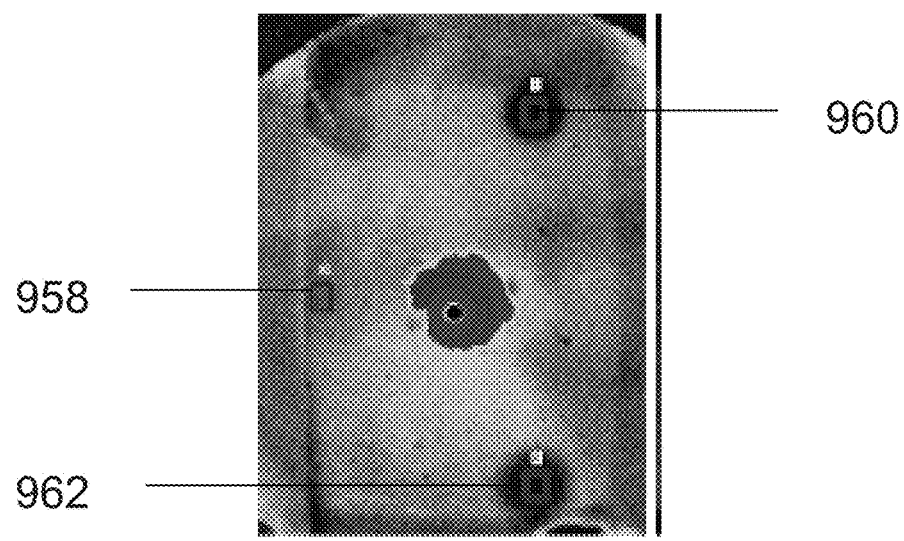
FIG. 9G is an infrared (IR) image of the sample with four layers of tape on the sample.
Figure 9H:
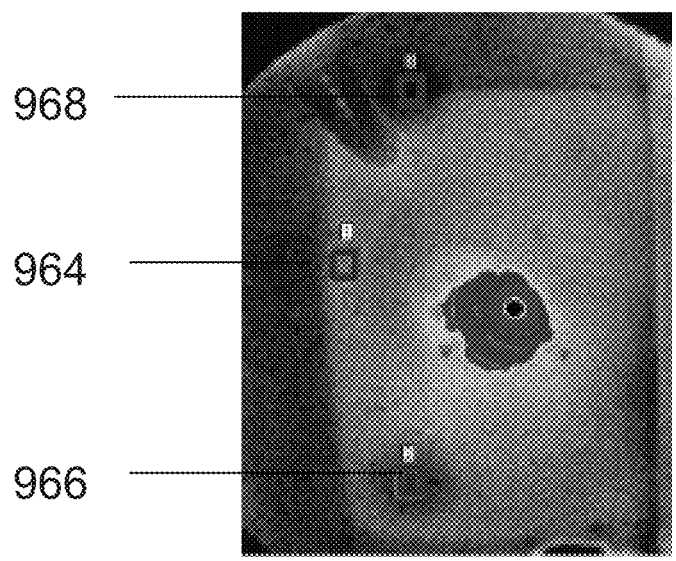
FIG. 9H is an infrared (IR) image of the sample with six layers of tape on the sample.
Figure 9I:
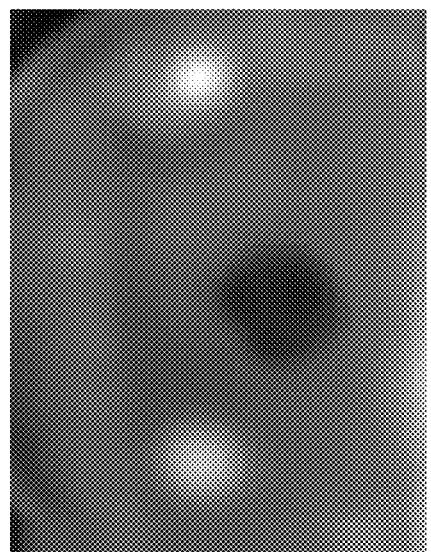
FIG. 9I is a processed image of the image shown in FIG. 9H.
Figure 9J:
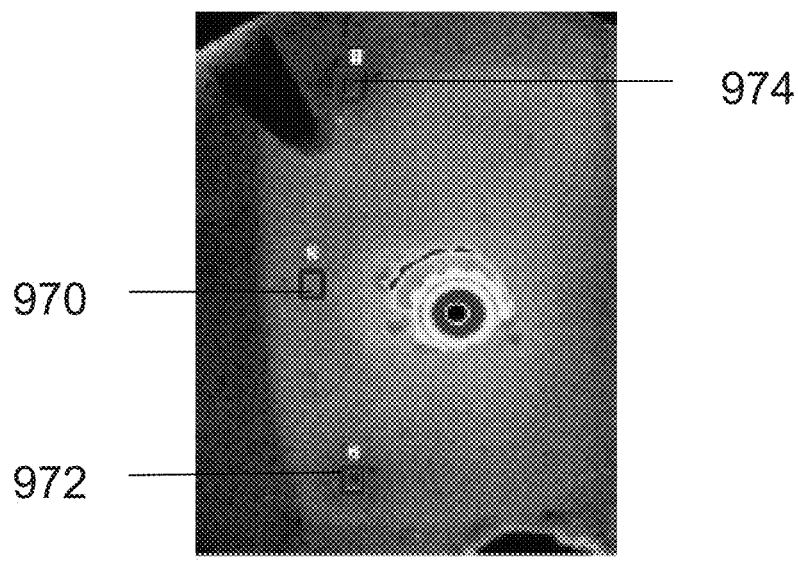
FIG. 9J is an infrared (IR) image of the sample with eight layers of tape on the sample.
Figure 9K:
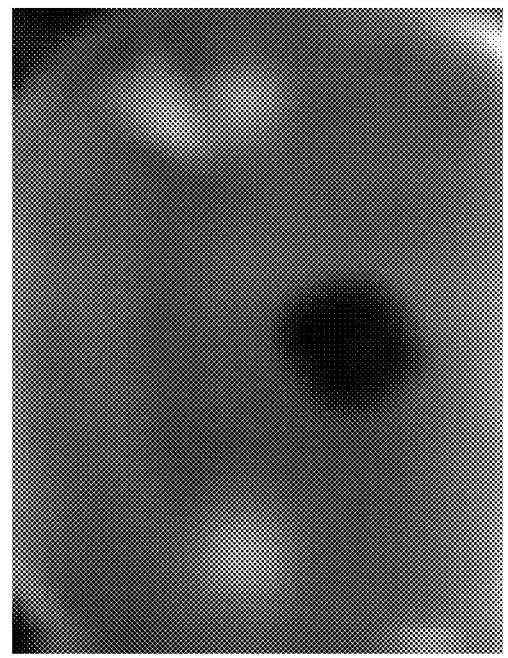
FIG. 9K is a processed image of the image shown in FIG. 9J.
Figure 9L:
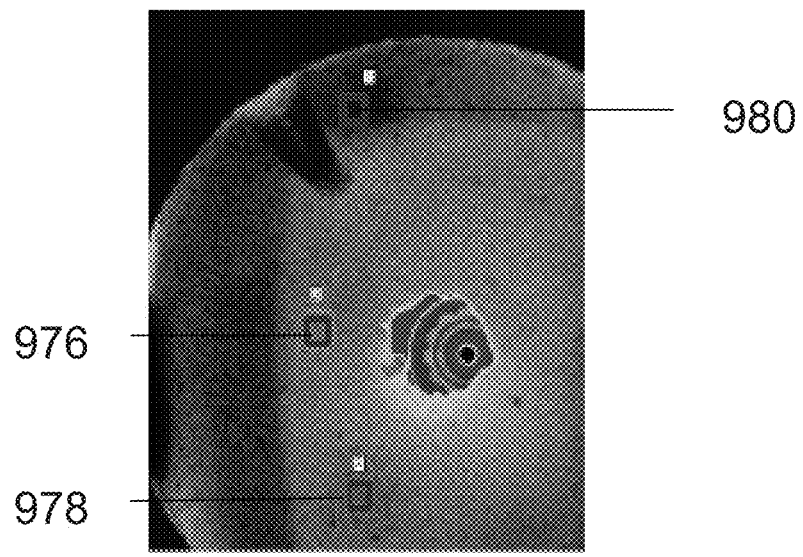
FIG. 9L is an infrared (IR) image of the sample with ten layers of tape on the sample.
Figure 9M:
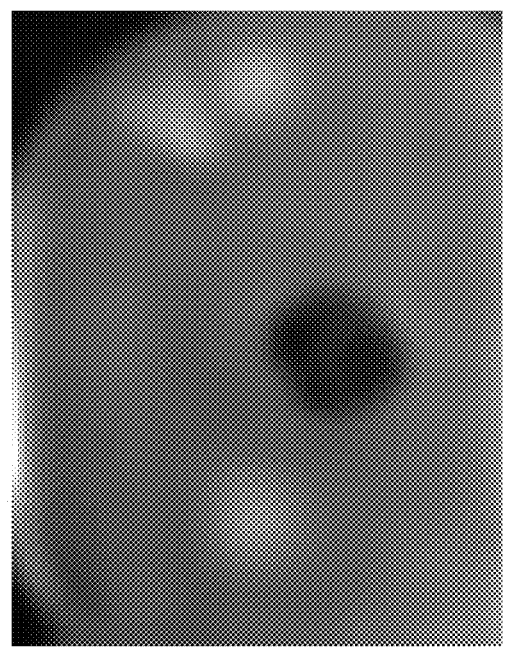
FIG. 9M is a processed image of the image shown in FIG. 9L.

FIG. 9F is an infrared (IR) image 900f of the sample with two layers of tape on the sample. 952 indicates an area of the sample with no defects, 954 indicates an area of the sample with a small defect and 956 indicates an area of the sample with a large defect. FIG. 9G is an infrared (IR) image 900g of the sample with four layers of tape on the sample. 958 indicates an area of the sample with no defects, 960 indicates an area of the sample with a small defect and 962 indicates an area of the sample with a large defect. FIG. 9H is an infrared (IR) image 900h of the sample with six layers of tape on the sample. 964 indicates an area of the sample with no defects, 966 indicates an area of the sample with a small defect and 968 indicates an area of the sample with a large defect. FIG. 9I is a processed image 900i of the image shown in FIG. 9H, so that two defects can be observed more clearly. FIG. 9J is an infrared (IR) image 900j of the sample with eight layers of tape on the sample. 970 indicates an area of the sample with no defects, 972 indicates an area of the sample with a small defect and 974 indicates an area of the sample with a large defect. FIG. 9K is a processed image 900k of the image shown in FIG. 9J. FIG. 9L is an infrared (IR) image 900l of the sample with ten layers of tape on the sample. 976 indicates an area of the sample with no defects, 978 indicates an area of the sample with a small defect and 980 indicates an area of the sample with a large defect. FIG. 9M is a processed image 900m of the image shown in FIG. 9L. There may be strong interference due to reflections of the camera and other parts of the setup as observed from the infrared images. However, with the help of image process software, direct visibility may be extended beyond 10 layers.

The transient temperature behavior of three regions may observed, which correspond to: 1) area without a defect; 2) small defect and; 3) large defect. It can be seen that even fewer than 10 layers of masking tape the contrast between the region without defect (marked as empty in figure below) and regions with defects are still measurable. At the same time, the temperature behavior of defects with different sizes may also be distinguished. The temperature drop is in the range of 0.7° C. This is smaller than the predicted from ideal gas law above. As was mentioned, the value is determined by the competition of heat transfer to remaining slow molecules (FIG. 5B) and heat conduction from the bulk of the wall. It may be possible to improve this value by making the pressure change in the chamber in a faster way using electronically controlled valve placed much closer to the chamber. The deviation may come from the fact that there is still a radiation heat flux and that the pressure change is not instantaneous enough. In various embodiments, the reduction of pressure for dry samples may be carried out within time scales below 1 second.

One can see that the area without a defect has a different transient behavior in comparison with areas that contain defects. The difference between the small and large defect may also be measured. However, as expected, the time taken for maximum contrast between these two defects gets longer when the number of layers is increased.

Figure 10:
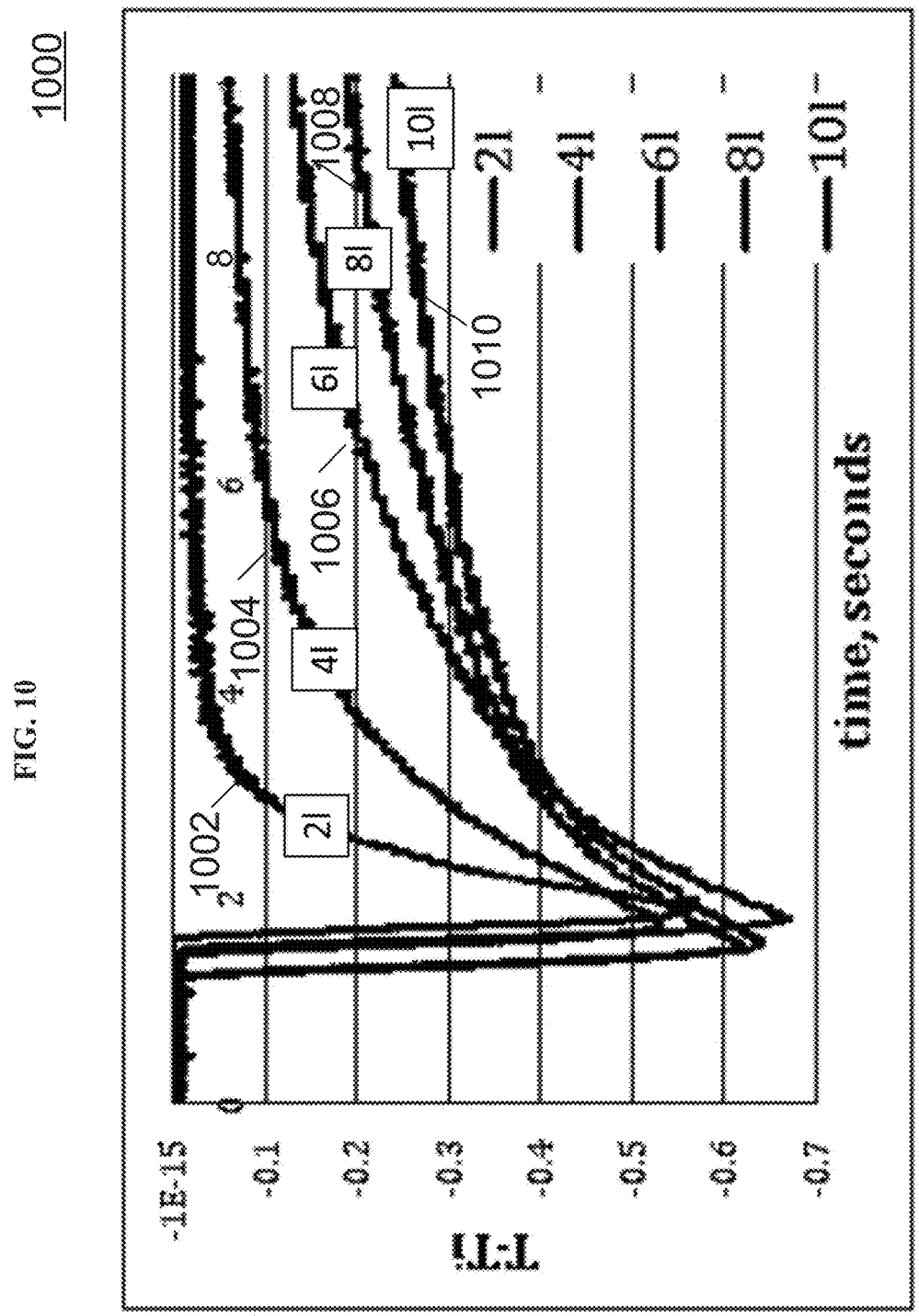
FIG. 10 is a plot of temperature change (K) as a function of time (s) illustrating the temperature curves for the area without a defect for different number of masking tape layers.

FIG. 10 is a plot 1000 of temperature change (K) as a function of time illustrating the temperature curves for the area without a defect for different number of masking tape layers. 1002 shows the temperature curve for an area covered with two layers, 1004 shows the temperature curve for an area covered with four layers, 1006 shows the temperature curve for an area covered with six layers, 1008 shows the temperature curve for an area covered with eight layers, and 1010 shows the temperature curve for an area covered with ten layers.

Various embodiments may be able to distinguish defects from sound areas with better sensitivity. Various embodiments may open a good opportunity for extraction of thermo-physical parameters of the sample. For this, the heat equation for the heat conduction from the bulk of the material may need to be solved.

Figure 11:
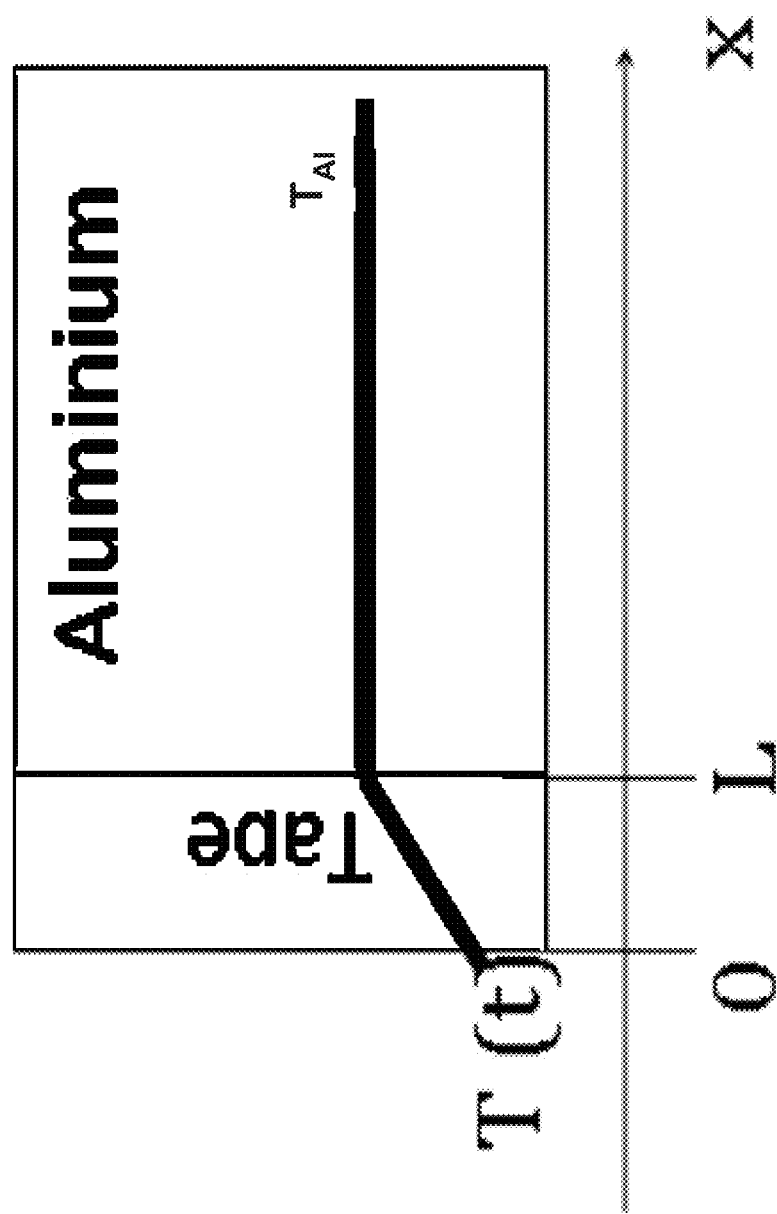
FIG. 11 is a schematic illustrating a linear temperature gradient of a within the overlying tape on the plate.

FIG. 11 is a schematic 1100 illustrating a linear temperature gradient of a within the overlying tape on the plate. An assumption is made here that after the cooling of the wall there is a linear gradient of temperature within the masking tape as shown in FIG. 11.

The heat equation may be provided by:

$$\frac{d^2 T}{dx^2} = \frac{1}{\alpha} \frac{dT}{dt} \quad (11)$$

where T is the temperature, t is the time and $$\alpha = \frac{\lambda}{c_p \rho} \quad (12)$$

$\lambda$ is the material conductivity, $\rho$ is density and $c_p$ is specific heat or thermal capacity.

The adiabatic boundary condition at the outside part of the tape may be provided by:

$$\frac{\partial T}{\partial x}(0, t) = 0 \quad (13)$$

This condition means that that this interface blocks any heat transfer from the wall to the surroundings. The rational here is that there is no air on the left side of the wall, so the heat cannot be transferred convectively. At the same time, heat transfer through IR radiation absorption and emission may be ignored. The possible contribution from radiative heating and its contribution to the final solution may be estimated to be fraction of a percent.

Temperature (T) of the interface between aluminum and tape is controlled by the temperature on both sides and respective effusivities and may be provided by:

$$T(L) = \frac{e_{Al} \times T_{Al} + e_{tape} \times T_{tape}}{e_{Al} + e_{tape}} \quad (14)$$

where $e_{Al}$ is the effusivity of aluminum and $e_{tape}$ is the effusivity of the tape, $T_{Al}$ is the temperature of aluminum and $T_{tape}$ is the temperature at the exposed end of the tape.

Effusivity may be provided by:

$$e = \sqrt{\rho c_p \lambda} \quad (15)$$

FIG. 12 is a table 1200 showing the thermo-physical parameters for aluminum, tape and air.

$$\text{Assuming} \frac{T_{Al}}{T_{tape}} \approx 1, \quad (16)$$

$$T(L, t) \approx T_{Al}$$

After cooling, a certain temperature distribution may be expected in the tape layer. For simplicity, this distribution may be modeled as linear with respect to x (as shown in FIG. 11) so the initial condition may be written as following:

$$T(x, 0) = T(0, 0)\left(1 - \frac{x}{L}\right) + T_{Al}\frac{x}{L} \quad (17)$$

Dimensionless units may be introduced as $$y = \frac{x}{L} \quad (18)$$

$$\theta = \frac{T_{Al} - T(x, t)}{T_{Al} - T(0, 0)} \quad (19)$$

$$p = \frac{t\alpha}{L^2} \quad (20)$$

Consequently, $$\frac{\partial^2 \theta}{\partial y^2} = \frac{\partial \theta}{\partial p} \quad (21)$$

With new boundary and initial conditions, $$\frac{\partial \theta}{\partial y}(0, p) = 0 \quad (22)$$

$$\theta(1, p) = 0 \quad (23)$$

$$\theta(y, 0) = 1 - y \quad (24)$$

Using method of separation of variables, $$\theta(y,p) = \mu(y) \times \nu(p) \quad (25)$$

Equation (21) becomes, $$\frac{\ddot{\mu}}{\mu} = \frac{\dot{v}}{v} = -y^2 \quad (26)$$

where y is a constant.

Since solution for $\theta$ is well-known, $$\theta(y,p) = [A\cos(yy) + B\sin(yy)]e^{-y^2 p} \quad (27)$$

From boundary condition as highlighted in Equation (22), B=0. Further, from boundary condition as highlighted in Equation (23), A cos(y)=0, hence $$y_n = \frac{1}{2}(2n - 1)\pi \quad (28)$$

$$\theta(y, 0) = \sum_1^\infty A_n \cos(y_n y) = 1 - y \quad (29)$$

In order to solve Equation (29), the following approach may be implemented. Multiplying both parts of Equation

(29) by $\cos(y_m d)$, where m is an integer, and integrating over the tape thickness. The right side will be:

$$\int_0^1 (1-y)\cos(y_m y) dy = \int_0^1 \cos(y_m y) dy - \int_0^1 y\cos(y_m y) dy$$

$$\int_0^1 y\cos(yy) dy = \frac{1}{y^2}[yy\sin(yy) + \cos(yy)]\Big|_0^1$$

$$= \frac{\sin y}{y} - \frac{1}{y^2}$$

$$\int_0^1 \cos(y_m y) dy = \left[\frac{\sin(yy)}{y}\right]_0^1 = \frac{\sin y}{y}$$

$$\int_0^1 (1-y)\cos(y_m y) dy = \frac{1}{y^2}$$

The left side of Equation (31) may be written as follows:

$$\sum_1^\infty A_n \int_0^1 \cos(y_n y)\cos(y_m y) dy$$

$$\int_0^1 \cos(y_n y)\cos(y_m y) dy = \begin{cases} 0, & n \neq m \\ \frac{1}{2}, & n=m \end{cases}$$

Hence, only the term with n=m remains in the summation.

$$A_m = \frac{2}{y_m^2} \qquad (30)$$

$$\theta(y, p) = \sum_1^\infty \frac{2}{y_n^2} \cos(y_n y) e^{-y_n^2 p} \qquad (31)$$

Solution for the surface temperature at y=0

$$\theta(0, p) = \sum_1^\infty \frac{2}{y_n^2} e^{-y_n^2 p} = \sum_1^\infty K_n \qquad (32)$$

The relationship for between two closest terms $K_1$ and $K_2$ in equation (32) may be estimated for different values of L. In the considered example the thickness of a masking tape is L≈80 µm. FIG. 13 is a table 1300 illustrating the relationship between these components at 0.01 seconds (sec), 0.1 seconds (sec) and 1 second (sec) after the start of the back-heating process. It can be seen from FIG. 13 that the second term $K_2$ is less that 10% of $K_1$ and thus, may be neglected. Equation (32) may be rewritten as $$\theta(0, t) = \frac{T_{Al} - T(0, t)}{T_{Al} - T(0, 0)} \qquad (33)$$

$$\approx \frac{8}{\pi^2} \exp\left[-\frac{\pi^2 \alpha t}{(2L)^2}\right]$$

$$\approx \exp[-\beta t]$$

The logarithm of Equation (35) allows the linearization of temperature changes with respect to time:

$$Ln(\theta(0,t)) \approx -\beta t \qquad (34)$$

Figure 14:
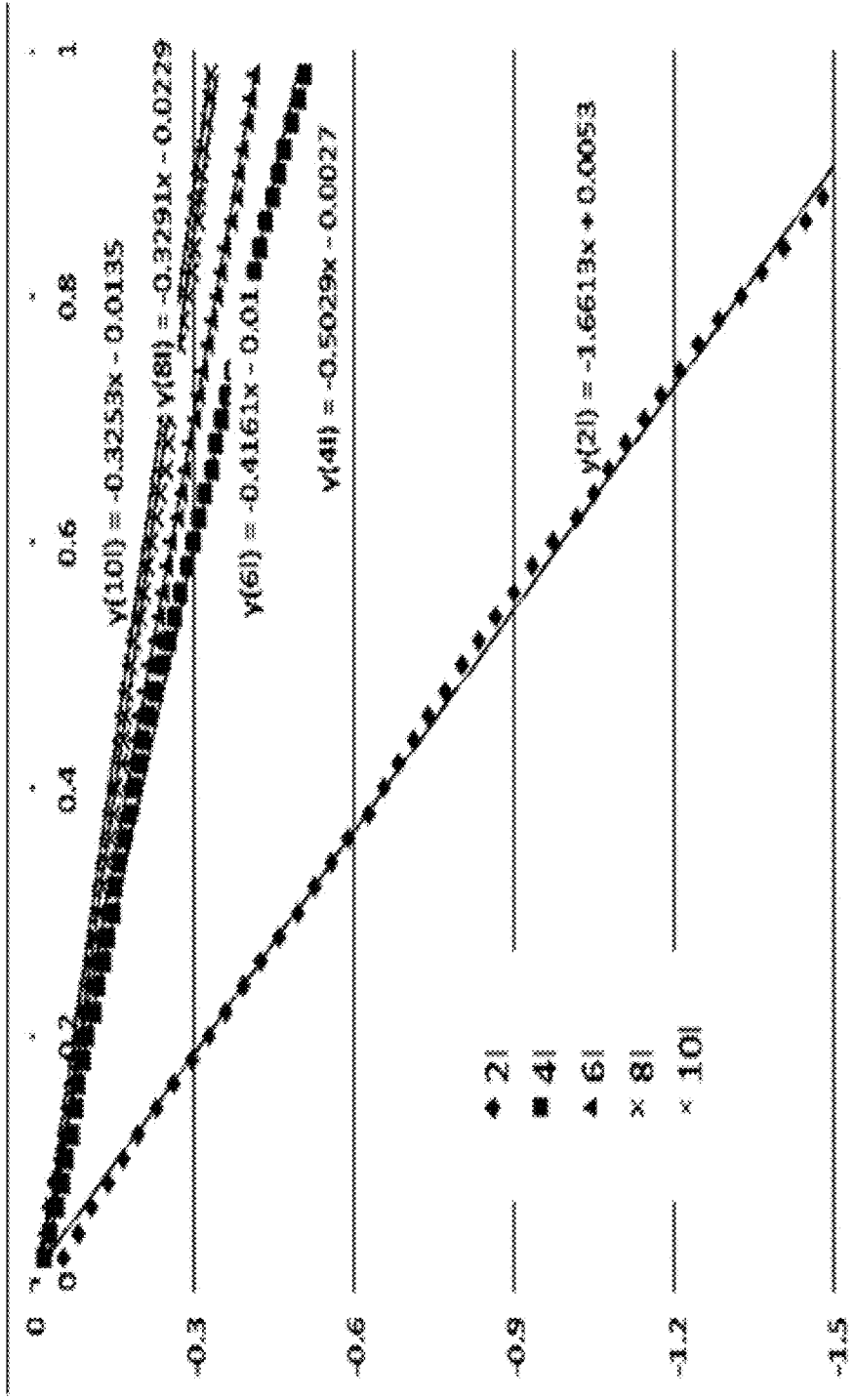
FIG. 14 is a plot of $Ln(\theta(0,t))$ plotted as a function of time (t).

FIG. 14 is a plot 1400 of $Ln(\theta(0,t))$ plotted as a function of t. FIG. 14 shows that for the $1^{st}$ second, the dependence for all curves is linear. According to Equation (35), the extracted gradient is a function of the number of layers.

$$\beta = \frac{\pi^2 \alpha}{(2L)^2} = \frac{\pi^2 \alpha}{(2nl)^2} \qquad (35)$$

where n is the number of layers and l is the thickness of one layer.

Figure 15A:
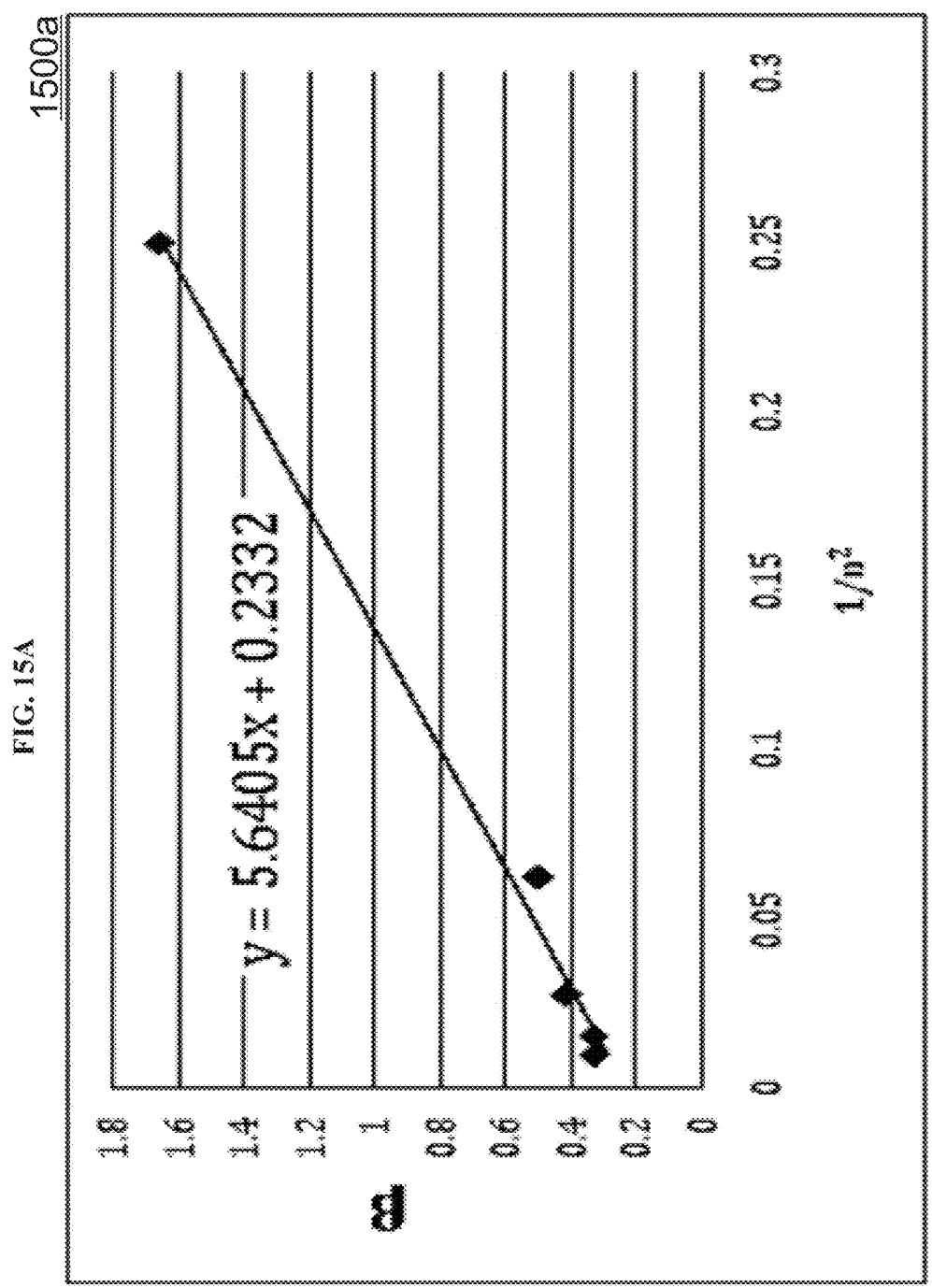
FIG. 15A is a plot of $\beta$ as a function of $1/n^2$ under original initial conditions.

FIG. 15A is a plot 1500a of β as a function of $1/n^2$ under original initial conditions. The gradient of the graph in FIG. 15A should be equal to $$\frac{\pi^2 \alpha}{(2l)^2}.$$

As can be seen from FIG. 15A, the slope of the line is 5.64. Taking l=80 um, diffusivity calculated will be $1.5*10^{-8}$ m²/s, which is 3.6 times smaller compared to the tabulated data in FIG. 14 but at least within the same order of magnitude.

Figure 15B:
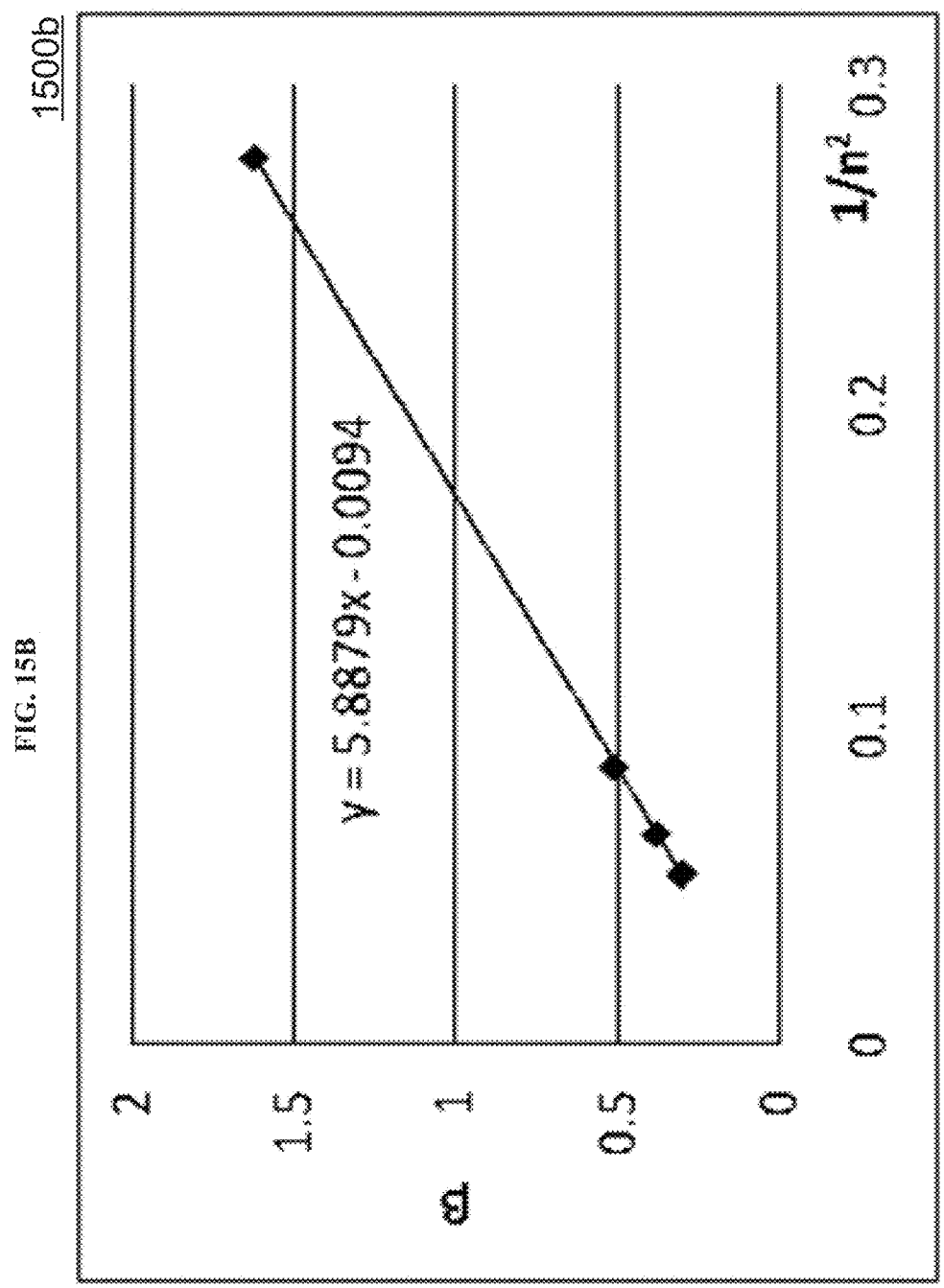
FIG. 15B is a plot of $\beta$ as a function of $1/n^2$ under adjusted initial conditions.
Figure 16A:
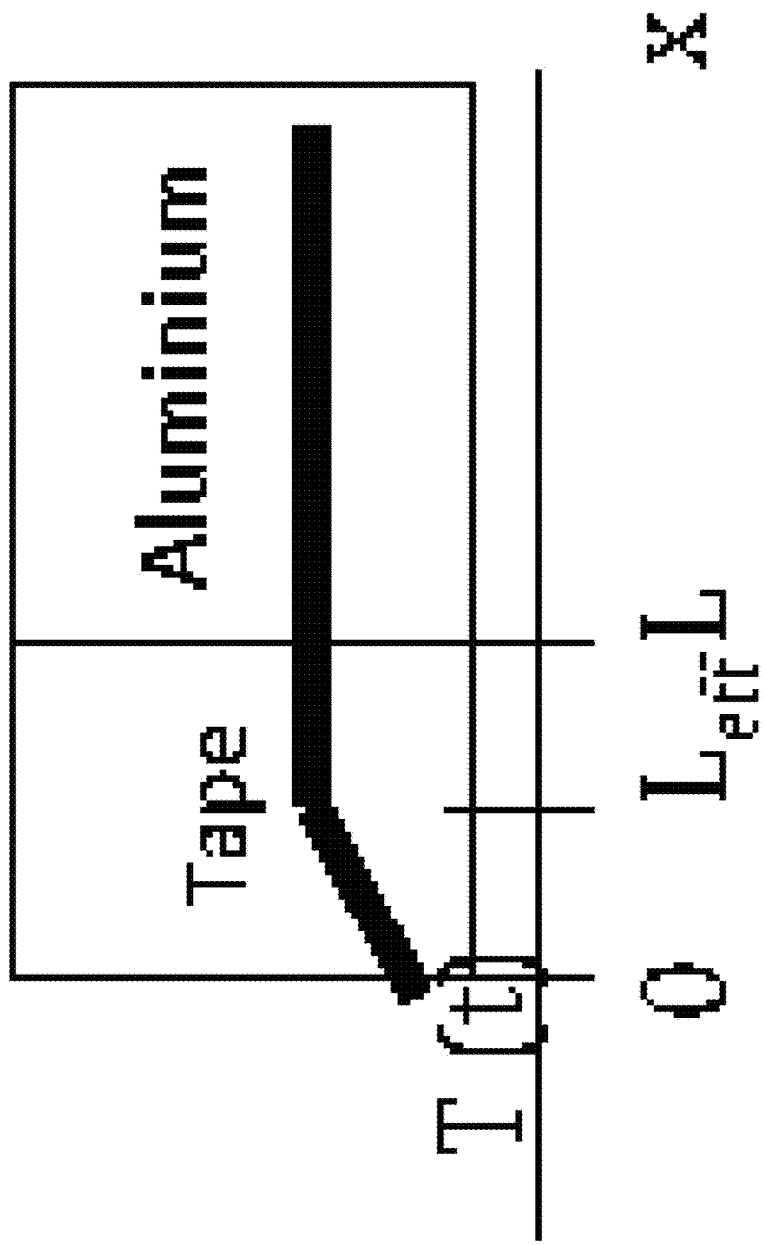
FIG. 16A is a schematic illustrating the temperature distribution inside the thick masking tape layer just after the cooling has stopped.
Figure 16B:
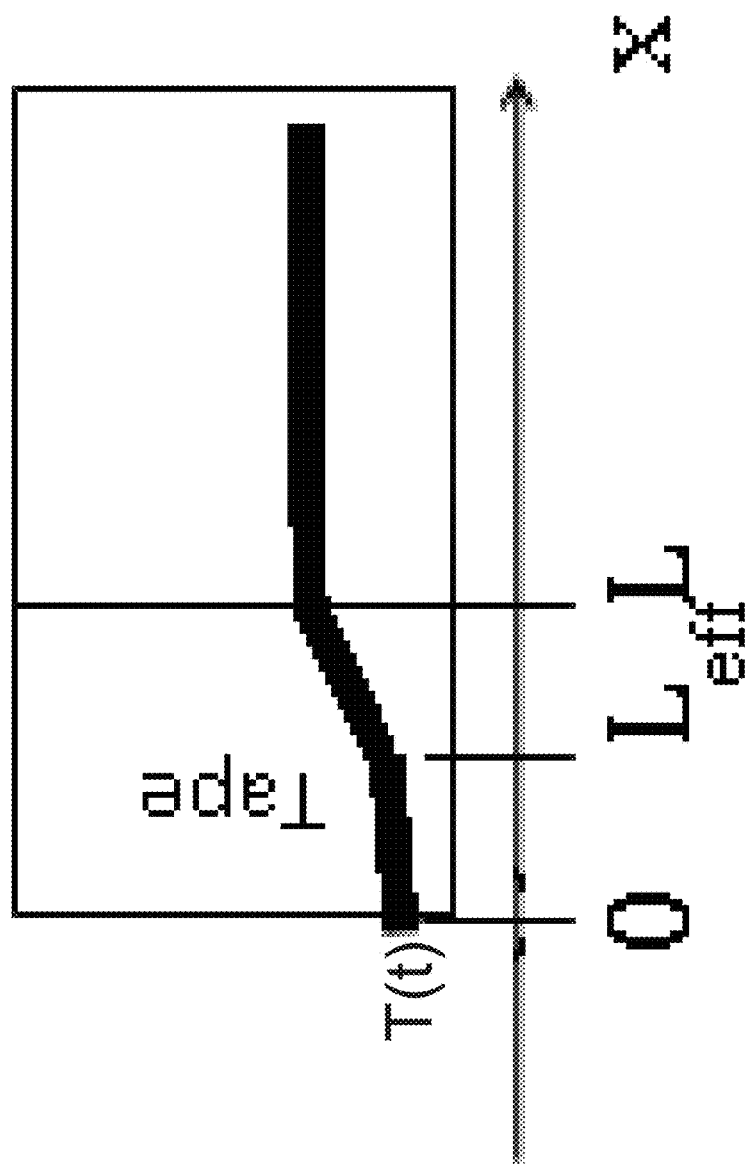
FIG. 16B is a schematic illustrating the temperature distribution inside the thick masking tape layer after the back heating has progressed.
Figure 16C:
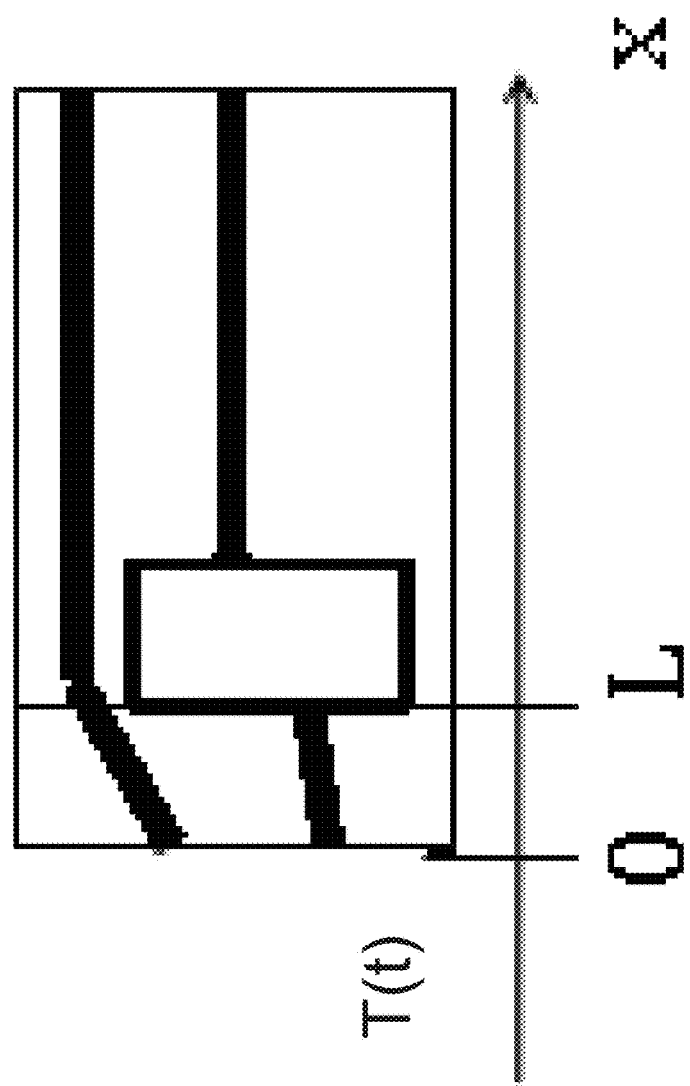
FIG. 16C is a schematic illustrating the temperature distribution inside the thick masking tape layer in the presence of a defect.
Figure 17:
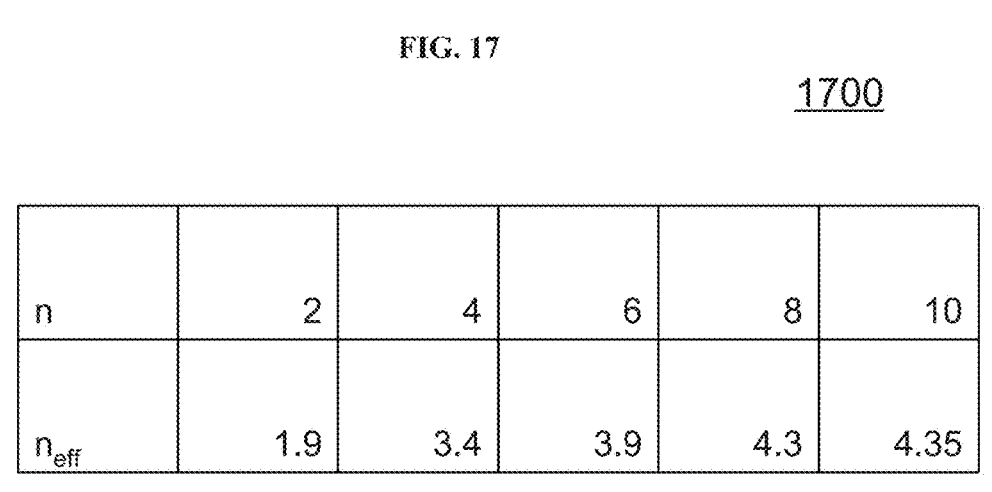

It may be noted from FIGS. 9A-E that for larger number of layers, the greater the delay for the temperature to return to the initial temperature value, i.e. the longer the time period for temperature to increase from the first temperature to the second temperature. The reason for this is may possibly be a different initial condition that was assumed in FIG. 11. FIG. 16A is a schematic 1600a illustrating the temperature distribution inside the thick masking tape layer just after the cooling has stopped. FIG. 16B is a schematic 1600b illustrating the temperature distribution inside the thick masking tape layer after the back-heating has progressed. FIG. 16C is a schematic 1600c illustrating the temperature distribution inside the thick masking tape layer in the presence of a defect. For thick layers, the low diffusivity of the tape may not allow the cold boundary to reach aluminum as shown in FIG. 16A. This means that the effective thickness of the layer cooled down may not be linearly proportional to the number of layers. By reducing the effective thickness, the new effective "n" may be deduced. It is also noted that this procedure may include gradually shifting the graph down in approximately parallel manner without a considerable change in slope. Hence, it may be inferred that the impact of reduced effective thickness is mainly manifested in the intercept of the ordinate axis at the value 0.23 in FIG. 15A. This intercept is supposed to be at β=0 according to Equation (34). Hence, a simple optimization may be performed by adjusting the value of n until the intercept is close to zero. FIG. 17 is a table 1700 illustrating the values of effective number of layers ($n_{eff}$) and the actual number of layers (n). As expected, the thickness of effectively cooled layer practically saturates after certain amount of layers, which coincides with the assumption in FIG. 16A. It is also noticed that the slope actually is increased slightly. However, it may not be enough to bridge the gap between the observed and theoretical value. This result may also not explain why the temperature does not return to the initial condition. The possible reasoning here is that during heating from the bulk of the thick tape the boundary condition given by Equation (16) is changing with time due to heat redistribution within the layer as shown in FIG. 16B. This effect may account for the slower than expected heating and it may be similar to the effects that are expected in the presence of defect as well. FIG. 15B is a plot 1500b of β as a function of $1/n^2$ under adjusted initial conditions.

Figure 18A:
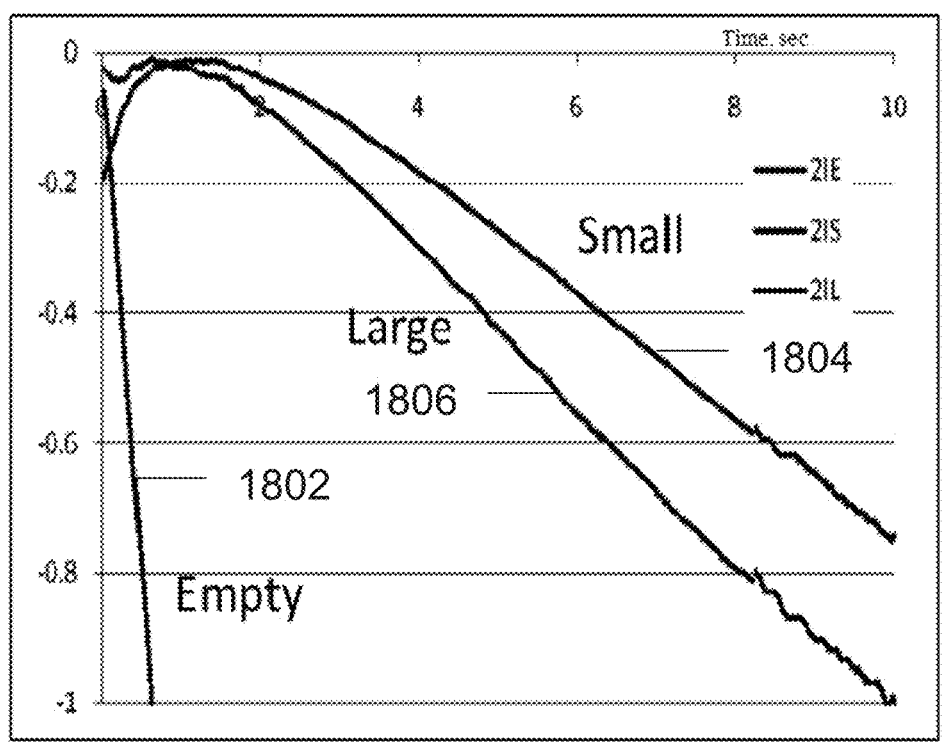
FIG. 18A is a plot of temperature change (kelvins or K) as a function of time (seconds or s) illustrating the temperature behaviors of a normal surface of the plate (no defect), the small defect and the large defect over time when two layers of masking tapes are covered over the plate.
Figure 18B:
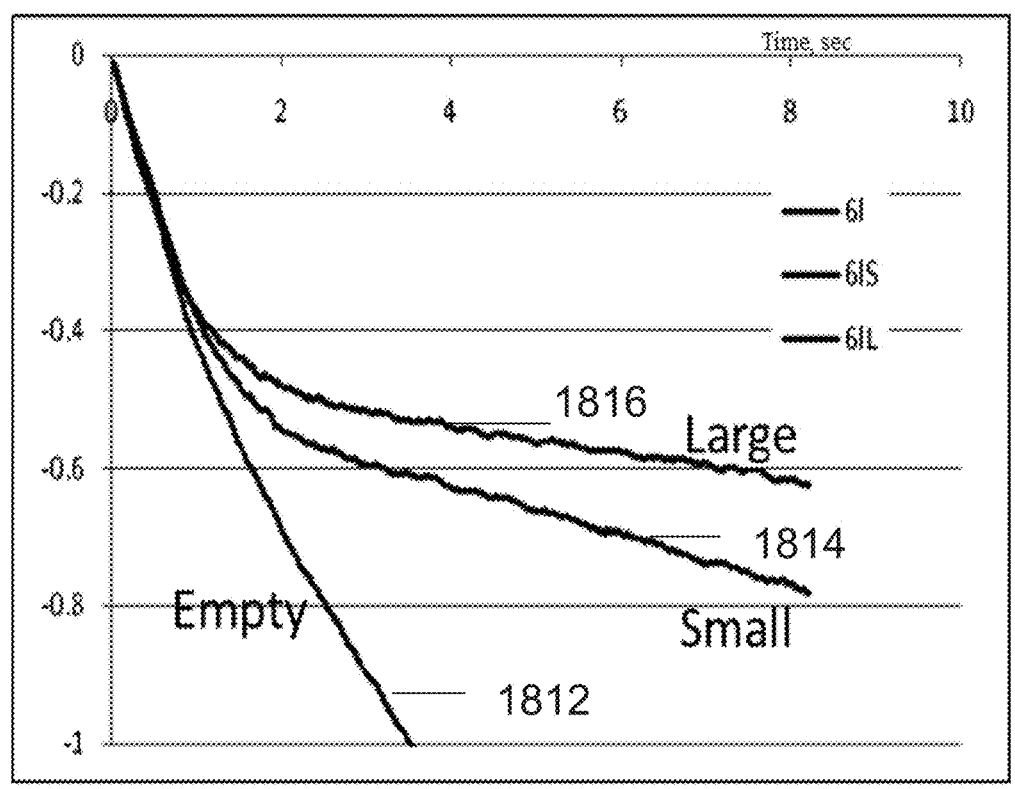
FIG. 18B is a plot of temperature change (kelvins or K) as a function of time (seconds or s) illustrating the temperature behaviors of a normal surface of the plate (no defect), the small defect and the large defect over time when six layers of masking tapes are covered over the plate.
Figure 18C:
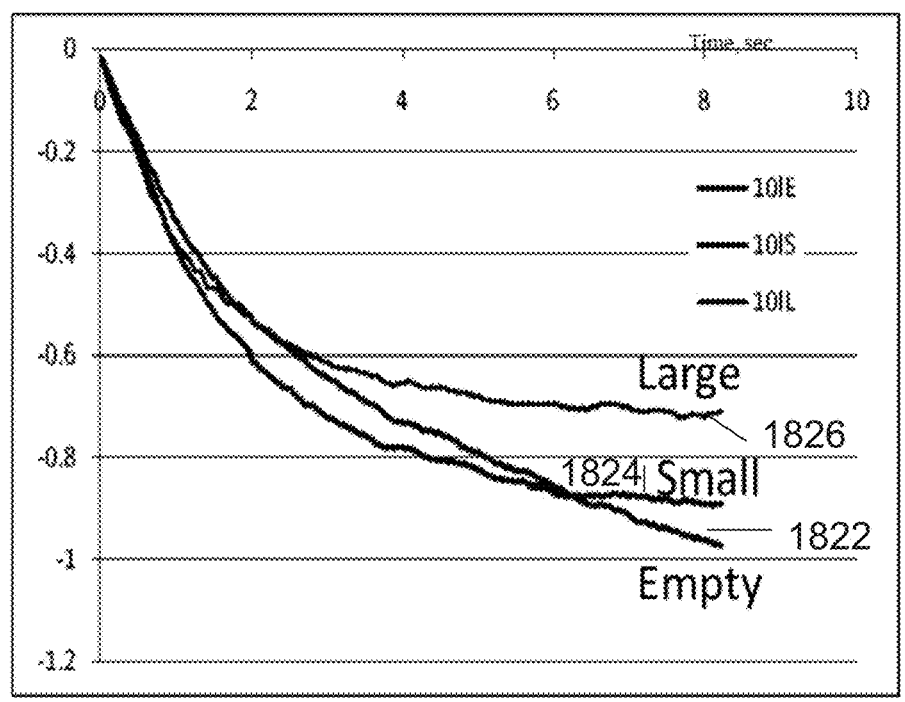
FIG. 18C is a plot of temperature change (kelvins or K) as a function of time (seconds or s) illustrating the temperature behaviors of a normal surface of the plate (no defect), the small defect and the large defect over time when ten layers of masking tapes are covered over the plate.

FIGS. 18A-C are plotted based on Equation (34). FIG. 18A is a plot 1800a of temperature change (K) as a function of time (s) illustrating the temperature behaviors of a normal surface of the plate (no defect, 1802), the small defect (1804) and the large defect (1806) over time when two layers of masking tapes are covered over the plate. FIG. 18B is a plot 1800b of temperature change (K) as a function of time (s) illustrating the temperature behaviors of a normal surface of the plate (no defect, 1812), the small defect (1814) and the large defect (1816) over time when six layers of masking tapes are covered over the plate. FIG. 18C is a plot 1800c of temperature change (K) as a function of time (s) illustrating the temperature behaviors of a normal surface of the plate (no defect, 1822), the small defect (1824) and the large defect (1826) over time when ten layers of masking tapes are covered over the plate.

Modifications may be introduced to improve the performance, such us 1) faster (electronic) pressure valve, 2) increase of the initial chamber pressure for achieving higher pressure differences, 3) use of gases that cool more and faster upon the expansion, similar to ones used in a fridge or an air-conditioned, and 4) distributed air connections for more uniform air flow and so on.

Figure 19A:
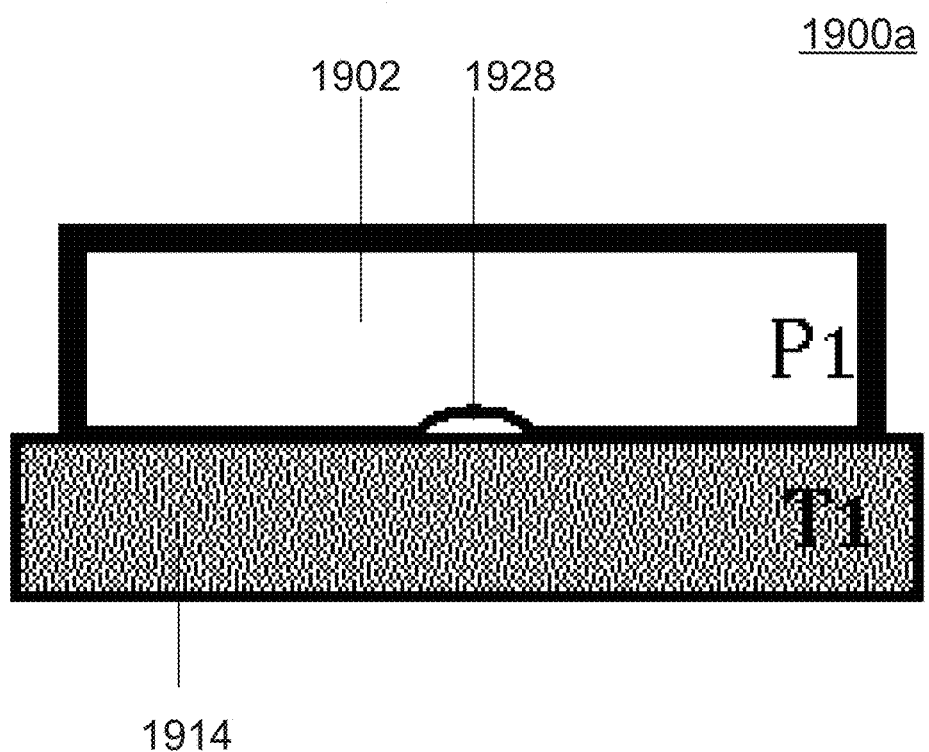
FIG. 19A is a schematic showing a chamber with sample forming a wall of the chamber prior to pressure reduction according to various embodiments.
Figure 19B:
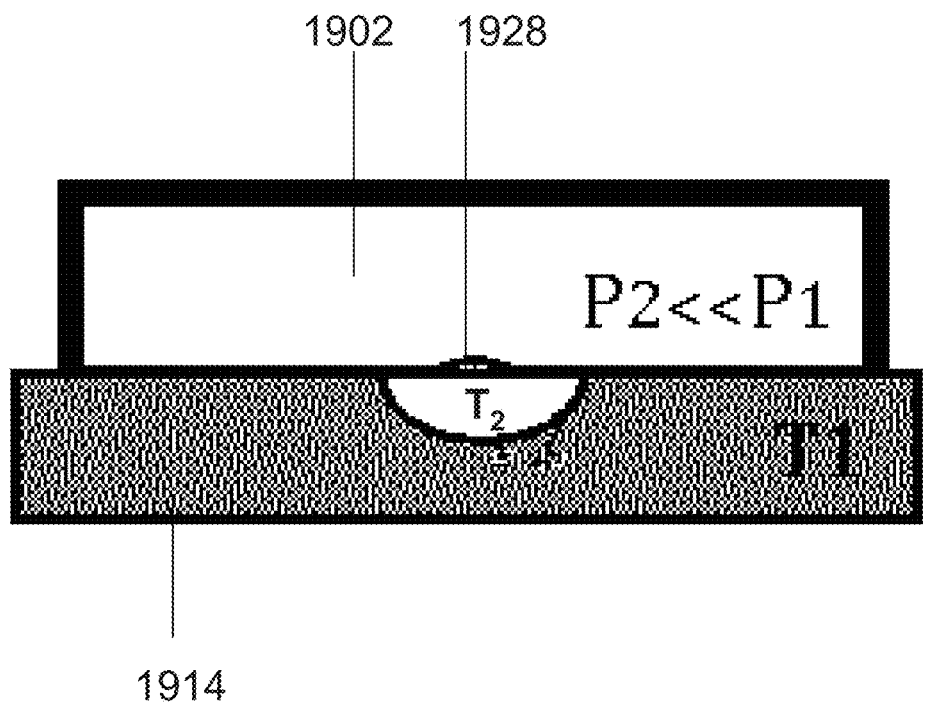
FIG. 19B is a schematic showing a chamber with sample forming a wall of the chamber after pressure reduction according to various embodiments.

FIG. 19A is a schematic 1900a showing a chamber 1902 with sample 1914 forming a wall of the chamber 1902 prior to pressure reduction according to various embodiments. FIG. 19B is a schematic 1900b showing a chamber 1902 with sample 1914 forming a wall of the chamber 1902 after pressure reduction according to various embodiments. According to various embodiments, the system may also be employed for moisture ingress detection. A chamber 1902 with water droplet on the wall 1914 (as shown in FIG. 19A) may be provided. The pressure in the chamber 1914 may then be reduced, i.e. from $P_1$ to $P_2$. The water droplet 1928 may then start to evaporate. Evaporation is an energy intensive process. The only source of energy (ignoring IR radiation) may be the heat from the wall 1914. Due to consumption of these heat, the wall region adjacent to the droplet 1928 may cool down (as shown in FIG. 19B). The temperature indicating the temperature may be due to a temperature increase from a first temperature to a second temperature. The first temperature may be due to a temperature drop from an initial temperature of the sample due to reduction in the pressure in the chamber. The temperature drop may be due to evaporation of water or fluid in the sample or on a surface of the sample. Various embodiments may be capable of detecting water ingress or fluid ingress into the micro cracks or along the designed discontinuities, like bolts and rivets. A defect such as a micro crack or a discontinuity may include water or fluid ingress.

Figure 20A:
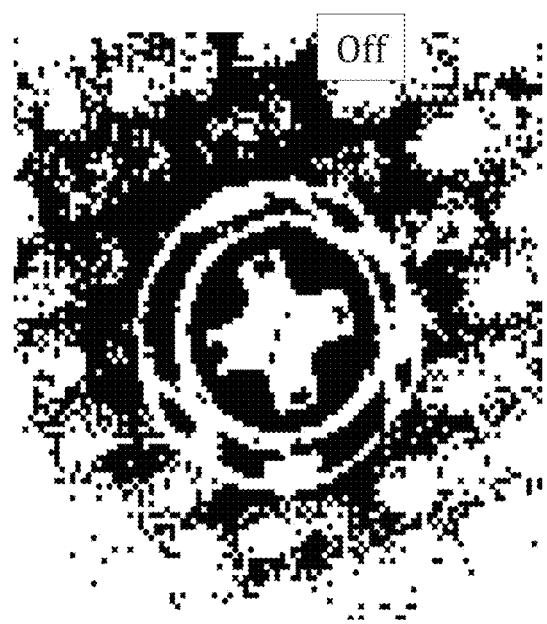
FIG. 20A is an infrared (IR) image of a dry bolt before pressure in the chamber is reduced.
Figure 20B:
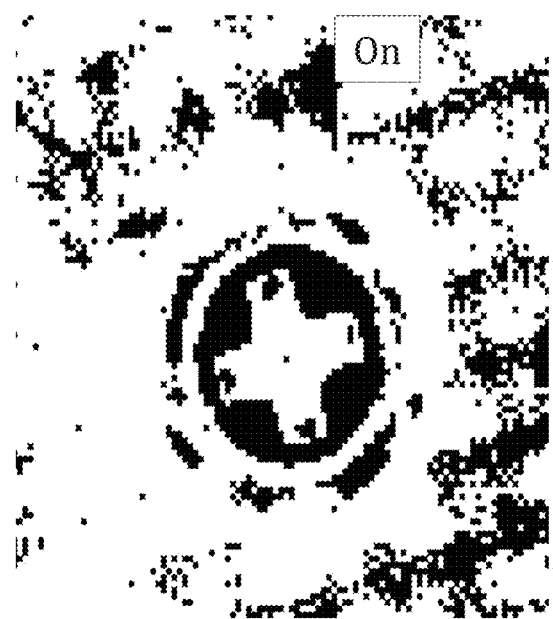
FIG. 20B is an infrared (IR) image of the dry bolt in FIG. 20A after pressure in the chamber is reduced.
Figure 20C:
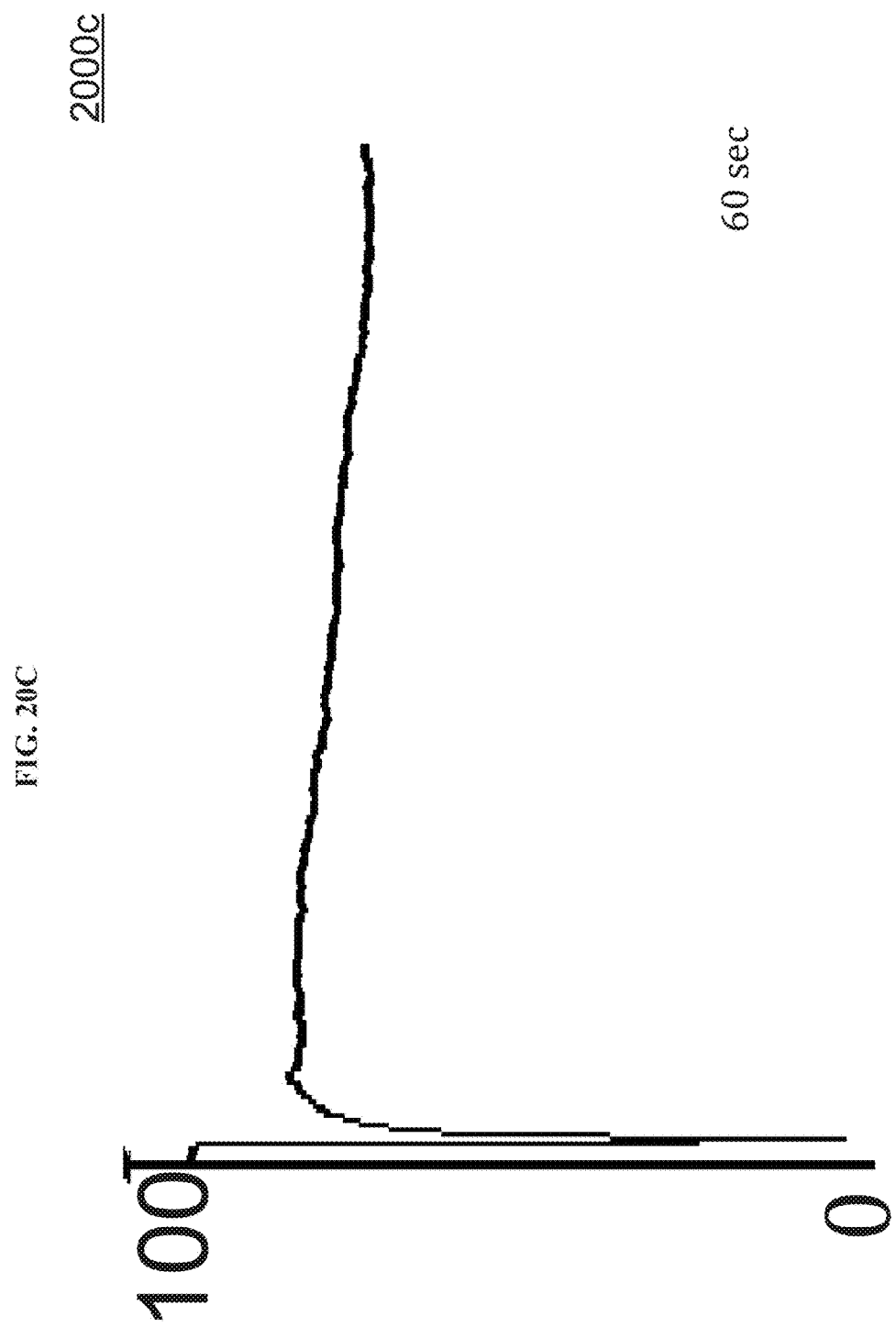
FIG. 20C is a graph of intensity value (arbitrary units) plotted as a function of time (in seconds or secs) illustrating variation of mean intensity value in the IR image of the dry bolt shown in FIGS. 20A-B over time.
Figure 20D:
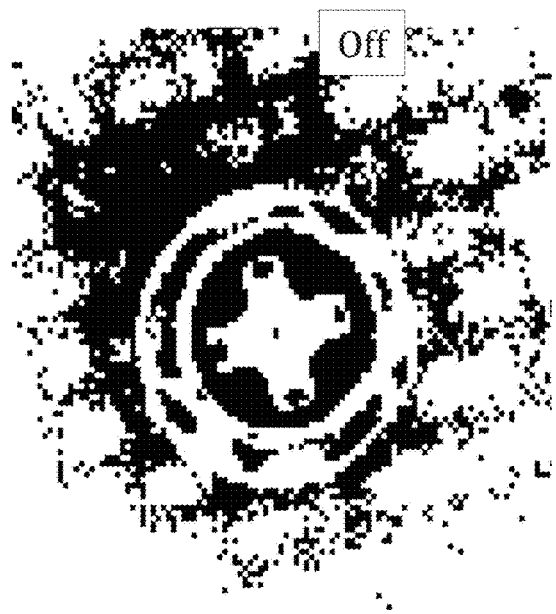
FIG. 20D is an infrared (IR) image of a wet bolt before pressure in the chamber is reduced.
Figure 20E:
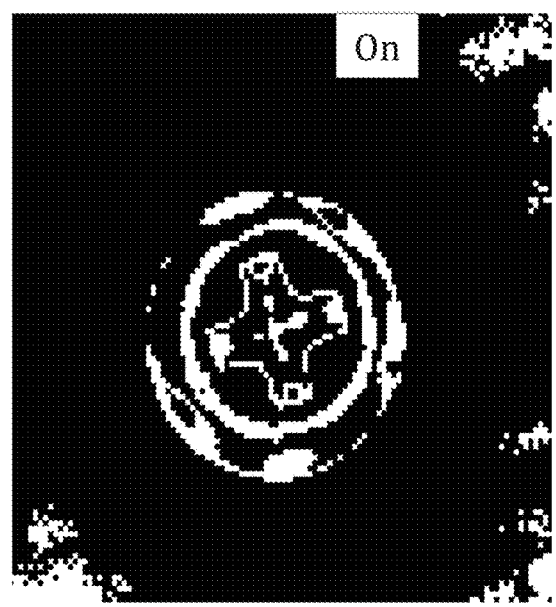
FIG. 20E is an infrared (IR) image of the wet bolt in FIG. 20D after pressure in the chamber is reduced.
Figure 20F:
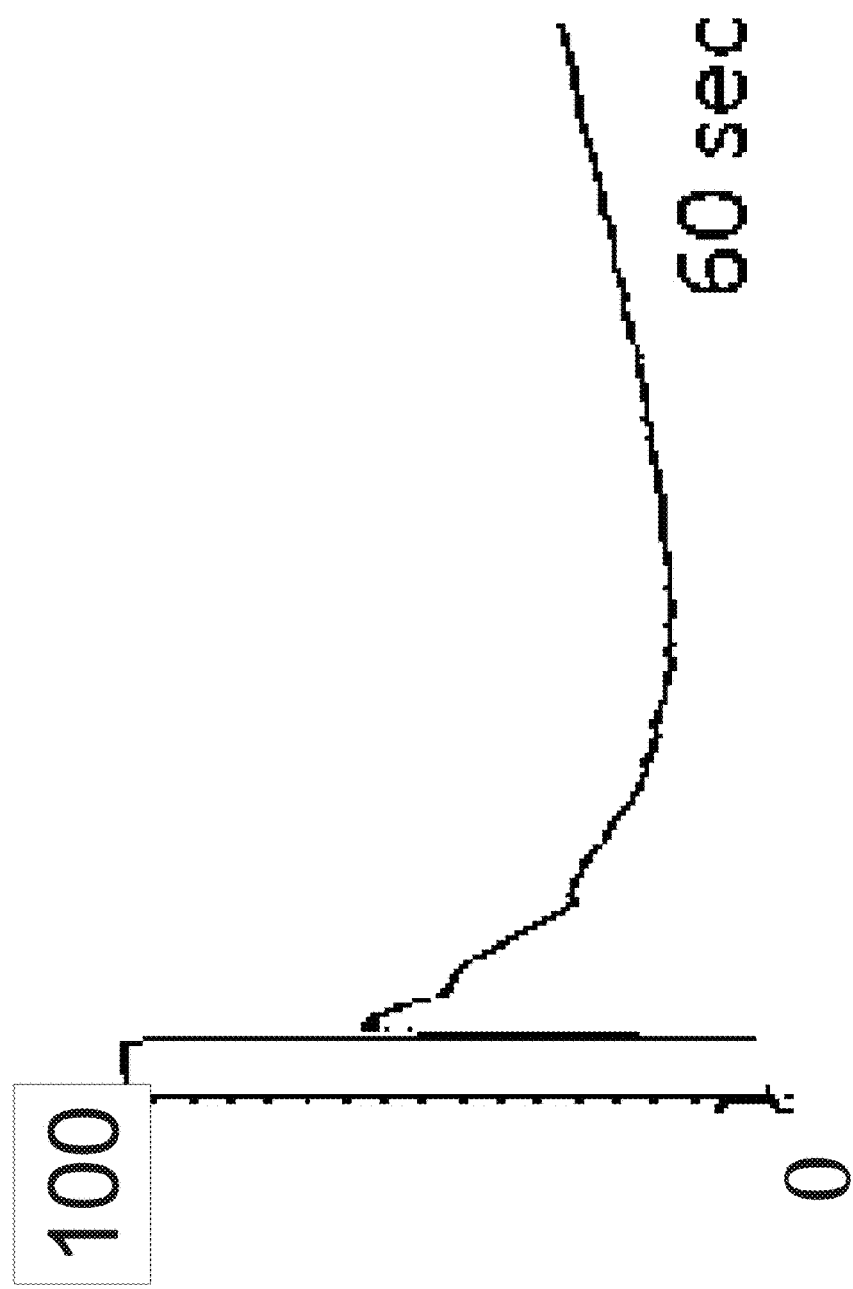
FIG. 20F is a graph of intensity value (arbitrary units) plotted as a function of time (in seconds or sec) illustrating variation of mean intensity value in the IR image of the wet bolt shown in FIGS. 20D-E over time.

The results of such application are demonstrated. FIG. 20A is an infrared (IR) image 2000a of a dry bolt before pressure in the chamber is reduced. FIG. 20B is an infrared (IR) image 2000b of the dry bolt in FIG. 20A after pressure in the chamber is reduced. FIG. 20C is a graph 2000c of intensity value (arbitrary units) plotted as a function of time (in seconds or sec) illustrating variation of mean intensity value in the IR image of the dry bolt shown in FIGS. 20A-B over time. FIG. 20D is an infrared (IR) image 2000d of a wet bolt before pressure in the chamber is reduced. FIG. 20E is an infrared (IR) image 2000e of the wet bolt in FIG. 20D after pressure in the chamber is reduced. FIG. 20F is a graph 2000f of intensity value (arbitrary units) plotted as a function of time (in seconds or sec) illustrating variation of mean intensity value in the IR image of the wet bolt shown in FIGS. 20D-E over time. The system according to various embodiments may be applied to a composite with a bolt going through it. In FIG. 20A, the bolt is dry. After the initial drop, the intensity detected quickly (within few seconds) returns towards the original value. In the case of the bolt with water ingress, the emission intensity behaves differently. As shown in FIGS. 20D-F, the surrounding of the bolt demonstrates dramatic decrease in the emission intensity, indicating drastic cooling. And the effect of cooling may be present for as long as 60 sec. This allows easy and reliable distinction between bolts with water ingress and without.

FIG. 21 is a schematic 2100 illustrating a method for detecting a defective sample according to various embodiments. The method may include reducing a pressure in a chamber. The method may include detecting the defective sample by detecting information indicating a temperature of the sample.

In other words, a method of detecting defects in a sample may be provided. The method may include reducing pressure within a chamber. The method may further include detecting information indicating a temperature of the sample.

Figure 22:
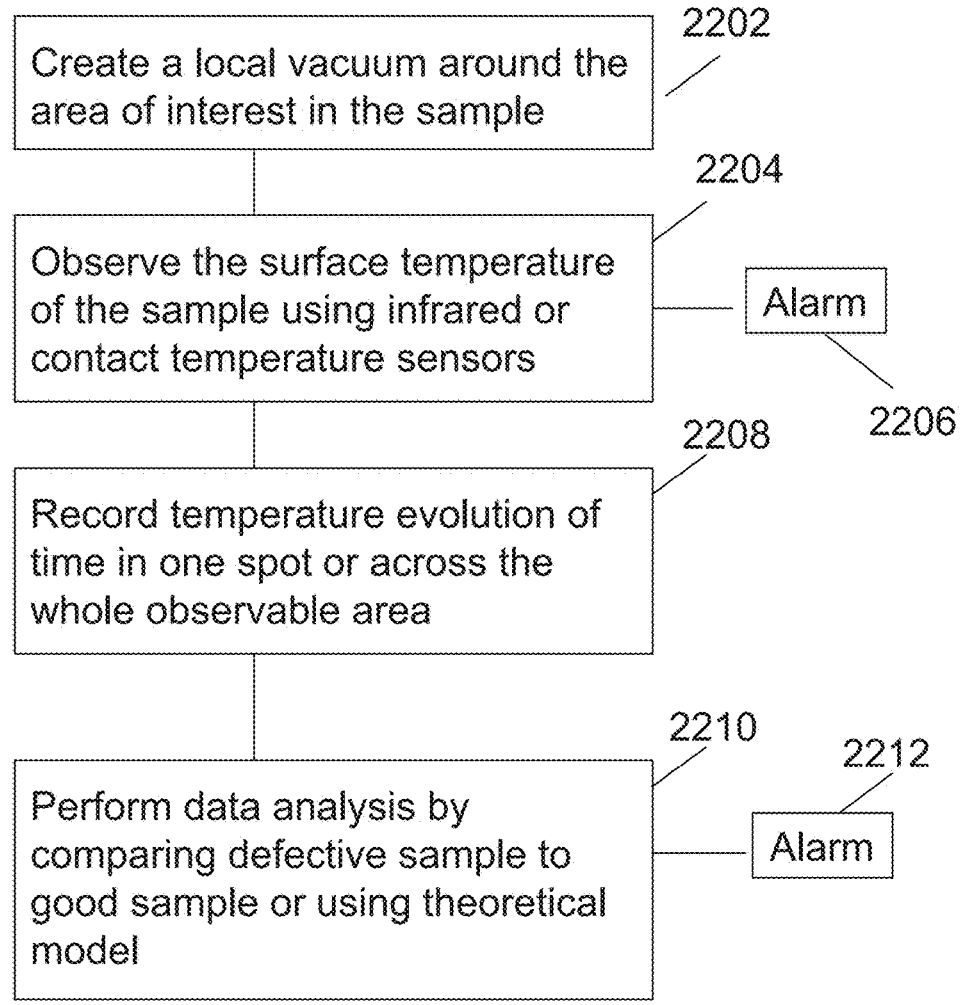
FIG. 22 is a schematic illustrating a method for detecting a defective sample according to various embodiments.

FIG. 22 is a schematic 2200 illustrating a method for detecting a defective sample according to various embodiments. The method may include, in 2202, creating a local vacuum around the area of interest in the sample. The method may include, in 2204, observing the surface temperature of the sample using infrared or contact temperature sensors. This qualitative stage may already be used for alarm 2206 based on operator experience or pre-programmed threshold values of temperature in a measurement unit. The method may include, in 2208, recording temperature evolution of time in one spot or across the whole observable area. The method may include, in 2210, performing data analysis through comparison of recording data to data recorded on good samples or through comparison of recording data to physical models, like in Equation 35. This quantitative stage may be used for alarm 2212 based on operator experience or pre-programmed threshold values for critical parameters.

In various embodiments, a defective sample or a defective region in the defective sample may be detected by comparing the information indicating the temperature with a pre-defined relationship or a predefined physical model. For instance, a defective sample or a defective region may be determined via comparison with one or more of Equations 33-35 and/or via comparison one or more of FIGS. 18A-C.

The pressure may be reduced via a pressure reducing mechanism coupled with the chamber. The information indicating a temperature of the sample may be detected via a detector.

In various embodiments, the information indicating the temperature may include different rates of temperature increase from a first temperature to a second temperature. In various embodiments, the information indicating the defect may be due to a temperature increase from a first temperature to a second temperature. The first temperature may be due to a temperature drop from an initial temperature of the sample due to the reduction in the pressure (i.e. reducing the pressure) in the chamber (due to activating the pressure reduction mechanism). The second temperature may be approximately equal to initial temperature before vacuum condition is initiated.

When the pressure is reduced, the sample may be cooled from the initial temperature to the first temperature. The temperature of the sample may increase from the first temperature to the second temperature due to transfer of energy to the sample.

The temperature drop may be due to evaporation of water in the defective sample.

The method may further include coupling a further chamber to the chamber. The method may additionally include reducing a further pressure in the further chamber.

The further chamber may be larger than the chamber. For instance, the further chamber may be about ten times larger than the chamber.

The further chamber may be constantly kept at vacuum or near vacuum. The further pressure in the further chamber may be lower than the pressure in the chamber. The pressure in the chamber may be reduced by exposing the pressure in the chamber to the further pressure in the further chamber.

The further chamber may be coupled to the chamber such that or so that a valve mechanism is between the further chamber and the chamber. Reducing the pressure in the chamber may include switching the valve mechanism from a first position to a second position such that or so that the pressure in the chamber is exposed to the further pressure in the further chamber.

The valve mechanism may include a valve. The valve may be an electrically or electronically controlled valve.

The valve may be a mechanical valve or a pneumatic valve.

The method may further include increasing the pressure in the chamber prior to exposing the pressure in the chamber to the further pressure in the further chamber.

The further chamber may include a liquid separator.

The further pressure of the further chamber may be reduced to be lower that the pressure of the chamber by a vacuum pump.

Detecting the defective sample further may include comparing the information indicating the temperature of the defective sample with further information indicating a temperature of a non-defective sample.

Detecting the defective sample may alternatively include detecting a differential rate of increase in temperature between a defective region and a non-defective region.

The chamber may include a gas. The gas may be selected from any one of a chlorofluorocarbon gas, a hydrofluorocarbon gas, a hydrochlorofluorocarbon gas, a carbon dioxide gas, a methyl chloride gas and an ammonia gas.

Detecting the information indicating the temperature may include detecting electromagnetic radiation emitted by the sample using a detector. The electromagnetic radiation may be transmitted through at least a portion of the chamber. The chamber may include a window. The window may be configured to allow electromagnetic radiation emitted by the sample to the detector. The chamber may further include an antireflection coating on the window. The coating may be configured to allow electromagnetic radiation matching a spectral range of the detector to the detector.

The window may be selected from a group consisting of a silicon window, a zinc selenide window and a germanium window. The electromagnetic radiation may be infrared radiation.

In various embodiments, detecting the information indicating the temperature of the sample may include contacting a detector with the sample. The detector may be a thermocouple.

The system may have one or more alarms that may indicate the presence of defect.

The system may include a data recording and data processing unit (or a data recording unit). The data recording and data processing unit (or data recording unit) may be coupled to the detector. The one or more alarms may be coupled to the data recording and data processing unit. The data recording and data processing unit (or data recording unit) may be configured to record temperature and/or pressure.

The method may include holding the chamber to the sample. The chamber may be held to the sample such that or so that a surface of the sample is cooled by the reduction in the pressure of the chamber.

The defective region may include a defect. The defect may include moisture ingress. The information indicating the temperature may be due to a temperature increase from a first temperature to a second temperature. The first temperature may be due to a temperature drop from an initial temperature of the sample due to the reduction in the pressure in the chamber. The temperature drop may be due to evaporation of water in the defective sample.

Methods described herein may further contain analogous features of any system or device described herein. Correspondingly, systems or devices described herein may further contain analogous features of any methods described herein.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A system for detecting a defective sample, the system comprising:
    a chamber with an open side, wherein the chamber is configured to attach to the defective sample at the open side of the chamber such that a volume is enclosed by the chamber and the defective sample;
    a pressure reducing mechanism coupled with the chamber;
    a detector; and
    a pressure sensor; wherein the pressure reducing mechanism is configured to reduce a pressure in the volume enclosed by the chamber and the defective sample, thereby causing a temperature drop from an initial temperature of the defective sample to a first temperature;
    wherein the detector is configured to detect information indicating a temperature of the defective sample, the information indicating the temperature due to a temperature increase from the first temperature to a second temperature, for detecting the defective sample; and
    wherein the pressure sensor is configured to sense the reduction in the pressure.

2. The system according to claim 1,
    wherein the second temperature is an ambient temperature.

3. The system according to claim 1,
    wherein the temperature drop is due to evaporation of water in the defective sample or on a surface of the defective sample.

4. The system according to claim 1,
    wherein the pressure reducing mechanism comprises:
    a further chamber coupled to the chamber; and a further pressure reducing mechanism coupled to the further chamber.

5. The system according to claim 4, wherein the further chamber is constantly kept at vacuum by the further pressure reducing mechanism.

6. The system according to claim 4, wherein the further pressure reducing mechanism is configured to reduce a further pressure in the further chamber to be lower than the pressure in the volume enclosed by the chamber and the defective sample.

7. The system according to claim 6, wherein the reduction of the pressure in the volume enclosed by the chamber and the defective sample is caused by exposure of the pressure in the enclosed volume to the further pressure in the further chamber.

8. The system according to claim 7, the system further comprising:
a valve mechanism;
wherein the further chamber is coupled to the chamber such that the valve mechanism is between the further chamber and the chamber;
wherein the valve mechanism is configured to be switched between a first position and a second position such that the switching of the valve mechanism from the first position to the second position causes the exposure of the pressure in the volume enclosed by the chamber and the defective sample to the further pressure in the further chamber.

9. The system according to claim 8, wherein the valve mechanism comprises a valve.

10. The system according to claim 7, wherein the chamber is configured such that the pressure in the volume enclosed by the chamber and the defective sample is increased prior to exposure of the pressure in the enclosed volume to the further pressure in the further chamber.

11. The system according to claim 4, wherein the further chamber comprises a liquid separator.

12. The system according to claim 4, wherein the further pressure reducing mechanism comprises a vacuum pump.

13. The system according to claim 1, wherein the defective sample is detected by comparing the information indicating the temperature of the defective sample with further information indicating a temperature of a non-defective sample.

14. The system according to claim 1, wherein a defective region in the defective sample is detected by detecting a differential rate of increase in temperature between the defective region and a non-defective region.

15. The system according to claim 1, wherein the detector is configured to detect the information indicating the temperature by detecting electromagnetic radiation emitted by the defective sample.

16. The system according to claim 15, wherein the electromagnetic radiation is transmitted through at least a portion of the volume enclosed by the chamber and the defective sample.

17. The system according to claim 15, wherein the electromagnetic radiation is infrared radiation.

18. The system according to claim 1, further comprising:
a data-recording unit coupled to the pressure sensor and the detector;
wherein the data-recording unit is configured to record the temperature increase and the pressure.

19. A method for detecting a defective sample, the method comprising:
reducing a pressure in a volume enclosed by a chamber and the defective sample using a pressure reducing mechanism coupled with the chamber, thereby causing a temperature drop from an initial temperature of the defective sample to a first temperature, wherein the chamber has an open side and the chamber is configured to attach to the defective sample at the open side of the chamber;
sensing the reduction in the pressure using a pressure sensor; and
detecting the defective sample by detecting information indicating a temperature of the defective sample, the information indicating the temperature due to a temperature increase from the first temperature to a second temperature, using a detector.

20. The method according to claim 19, further comprising:
recording the temperature increase and the pressure using a data-recording unit coupled to the pressure sensor and the detector.

* * * * *